(12) United States Patent
Kim et al.

(10) Patent No.: US 10,170,706 B2
(45) Date of Patent: Jan. 1, 2019

(54) AMINE-BASED COMPOUND AND ORGANIC LIGHT-EMITTING DEVICE INCLUDING THE SAME

(71) Applicant: Samsung Display Co., Ltd., Yongin, Gyeonggi-Do (KR)

(72) Inventors: Mi-Kyung Kim, Yongin (KR); Dong-Hyun Kim, Yongin (KR); Se-Hun Kim, Yongin (KR); Hwan-Hee Cho, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 597 days.

(21) Appl. No.: 14/668,815

(22) Filed: Mar. 25, 2015

(65) Prior Publication Data

US 2015/0280134 A1 Oct. 1, 2015

(30) Foreign Application Priority Data

Mar. 26, 2014 (KR) .................. 10-2014-0035373

(51) Int. Cl.
| | | |
|---|---|---|
| *H01L 51/00* | (2006.01) | |
| *C07D 209/86* | (2006.01) | |
| *H01L 51/50* | (2006.01) | |

(52) U.S. Cl.
CPC ........ *H01L 51/0072* (2013.01); *C07D 209/86* (2013.01); *H01L 51/006* (2013.01); *H01L 51/0058* (2013.01); *H01L 51/5056* (2013.01)

(58) Field of Classification Search
CPC ................................................ H01L 51/0061
See application file for complete search history.

(56) References Cited

U.S. PATENT DOCUMENTS

| | | | |
|---|---|---|---|
| 2005/0221124 A1 | 10/2005 | Hwang et al. | |
| 2009/0160323 A1* | 6/2009 | Nomura ............... | C07D 209/86 313/504 |
| 2011/0089408 A1* | 4/2011 | Schmid .................. | C07F 1/005 257/40 |
| 2011/0127495 A1 | 6/2011 | Hong et al. | |
| 2011/0193074 A1 | 8/2011 | Lee et al. | |
| 2012/0091438 A1 | 4/2012 | Yabunouchi et al. | |
| 2014/0117329 A1 | 5/2014 | Lee et al. | |
| 2014/0183466 A1 | 7/2014 | Lee et al. | |
| 2014/0183495 A1 | 7/2014 | Lee et al. | |
| 2015/0325795 A1* | 11/2015 | Lee ....................... | C07D 209/82 257/40 |

FOREIGN PATENT DOCUMENTS

| | | |
|---|---|---|
| JP | 2011-1349 A | 1/2011 |
| KR | 10-2005-0097670 A | 10/2005 |
| KR | 10-2009-0051141 A | 5/2009 |
| KR | 10-2010-0039815 A | 4/2010 |
| KR | 10-2010-0099250 A | 9/2010 |
| KR | 10-2012-0022861 A | 3/2012 |
| KR | 10-2012-0119881 A | 10/2012 |
| KR | 10-2014-0057418 A | 5/2014 |
| KR | 10-2014-0085110 A | 7/2014 |
| KR | 10-2014-0085111 A | 7/2014 |
| WO | 2014 088284 * | 6/2014 |

* cited by examiner

*Primary Examiner* — Kuo Liang Peng
(74) *Attorney, Agent, or Firm* — Lewis Roca Rothgerber Christie LLP

(57) ABSTRACT

According to one or more embodiments of the present invention, an amine-based compound is represented by Formula 1 below:

Formula 1

11 Claims, 1 Drawing Sheet

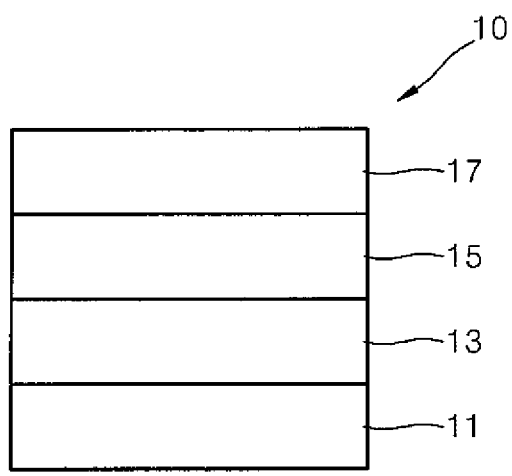

AMINE-BASED COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0035373, filed on Mar. 26, 2014, in the Korean Intellectual Property Office, the disclosure of which is incorporated herein in its entirety by reference.

BACKGROUND

1. Field

One or more embodiments relate to an amine-based compound and an organic light-emitting device including the same.

2. Description of the Related Art

Organic light-emitting devices are self-emission devices that have wide viewing angles, high contrast ratios, short response time, and excellent brightness, driving voltage, and response speed characteristics; and produce full-color images.

An organic light-emitting device may include a first electrode disposed on a substrate, and a hole transport layer, an emission layer, an electron transport layer, and a second electrode, which are sequentially disposed on the first electrode. Holes provided from the first electrode may move toward the emission layer through the hole transport layer, and electrons provided from the second electrode may move toward the emission layer through the electron transport layer. Carriers, such as holes and electrons, are combined in the emission layer to produce excitons. These excitons change from an excited state to a ground state, thereby generating light.

SUMMARY

Aspects according to one or more embodiments of the present invention are directed toward a novel amine-based compound and an organic light-emitting device including the same.

Additional aspects will be set forth in part in the description which follows and, in part, will be apparent from the description, or may be learned by practice of the presented embodiments.

According to one or more embodiments of the present invention, an amine-based compound is represented by Formula 1 below:

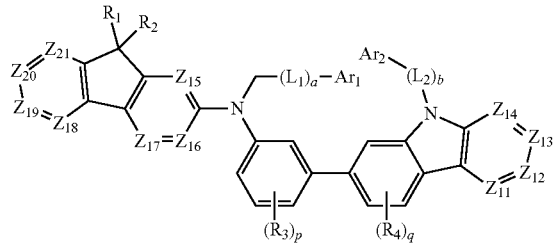

Formula 1 wherein in Formula 1, $Z_{11}$ is N or $C(R_{11})$, $Z_{12}$ is N or $C(R_{12})$, $Z_{13}$ is N or $C(R_{13})$, $Z_{14}$ is N or $C(R_{14})$, $Z_{15}$ is N or $C(R_{15})$, $Z_{16}$ is N or $C(R_{16})$, $Z_{17}$ is N or $C(R_{17})$, $Z_{18}$ is N or $C(R_{18})$, $Z_{19}$ is N or $C(R_{19})$, $Z_{20}$ is N or $C(R_{20})$, and $Z_{21}$ is N or $C(R_{21})$;

$L_1$ and $L_2$ may be each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic condensed heteropolycyclic group;

a and b are each independently an integer selected from 0 to 5;

$Ar_1$ and $Ar_2$ may be each independently a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted heteroaryl group, a substituted or unsubstituted monovalent non-aromatic condensed polycyclic group, or a substituted or unsubstituted monovalent non-aromatic condensed heteropolycyclic group;

$R_1$ to $R_4$ and $R_{11}$ to $R_{21}$ may be each independently a hydrogen atom, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_2$-$C_{60}$ heteroaryl group, a substituted or unsubstituted $C_6$-$C_{60}$ aryloxy group, a substituted or unsubstituted $C_6$-$C_{60}$ arylthio group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, or —$B(Q_6)(Q_7)$;

p is an integer selected from 1 to 4;

q is an integer selected from 1 to 3;

at least one substituent of the substituted $C_3$-$C_{10}$ cycloalkylene group, the substituted $C_2$-$C_{10}$ heterocycloalkylene group, the substituted $C_3$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_3$-$C_{10}$ cycloalkenyl group, the substituted $C_2$-$C_{10}$ heterocycloalkenyl group, the substituted $C_6$-$C_{60}$ aryl group, the substituted $C_2$-$C_{60}$ heteroaryl group, the substituted $C_6$-$C_{60}$ aryloxy group, the substituted $C_6$-$C_{60}$ arylthio group, the substituted monovalent non-aromatic condensed polycyclic group, and the substituted monovalent non-aromatic condensed heteropolycyclic group may be selected from:

a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), wherein $Q_1$ to $Q_7$, $Q_{11}$ to $Q_{17}$, $Q_{21}$ to $Q_{27}$, and $Q_{31}$ to $Q_{37}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_2$-$C_{60}$ heteroaryl group, a monovalent non-aromatic condensed polycyclic group, or a monovalent non-aromatic condensed heteropolycyclic group.

According to one or more embodiments of the present invention, an organic light-emitting device includes: a first electrode; a second electrode facing the first electrode; and an organic layer between the first electrode and the second electrode and including an emission layer, wherein the organic layer includes at least one of the amine-based compound described above.

BRIEF DESCRIPTION OF THE DRAWINGS

These and/or other aspects will become apparent and more readily appreciated from the following description of the embodiments, taken in conjunction with the drawing, which is a schematic view of an organic light-emitting device according to an embodiment.

DETAILED DESCRIPTION

Reference will now be made in more detail to embodiments, examples of which are illustrated in the accompanying drawing, wherein like reference numerals refer to like elements throughout. In this regard, the present embodiments may have different forms and should not be construed as being limited to the descriptions set forth herein. Accordingly, the embodiments are merely described below, by referring to the drawing, to explain aspects of the present description. Expressions such as "at least one of," when preceding a list of elements, modify the entire list of elements and do not modify the individual elements of the list. As used herein, the term "and/or" includes any and all combinations of one or more of the associated listed items. Further, the use of "may" when describing embodiments of the present invention refers to "one or more embodiments of the present invention."

An amine-based compound according to an embodiment is represented by Formula 1 below:

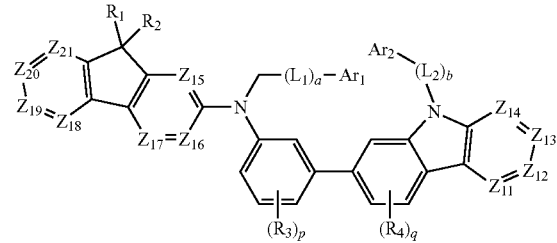

Formula 1 in Formula 1, $Z_{11}$ is N or C($R_{11}$), $Z_{12}$ is N or C($R_{12}$), $Z_{13}$ is N or C($R_{13}$), $Z_{14}$ is N or C($R_{14}$), $Z_{15}$ is N or C($R_{15}$), $Z_{16}$ is N or C($R_{16}$), $Z_{17}$ is N or C($R_{17}$), $Z_{18}$ is N or C($R_{18}$), $Z_{19}$ is N or C($R_{19}$), $Z_{20}$ is N or C($R_{20}$), and $Z_{21}$ is N or C($R_{21}$).

For example, in Formula 1, $Z_{11}$ may be C($R_{11}$), $Z_{12}$ may be C($R_{12}$), $Z_{13}$ may be C($R_{13}$), $Z_{14}$ may be C($R_{14}$), $Z_{15}$ may be C($R_{15}$), $Z_{16}$ may be C($R_{16}$), $Z_{17}$ may be C($R_{17}$), $Z_{18}$ may be C($R_{18}$), $Z_{19}$ may be C($R_{19}$), $Z_{20}$ may be C($R_{20}$), and $Z_{21}$ may be C($R_{21}$), but they are not limited thereto.

$L_1$ and $L_2$ in Formula 1 may be each independently a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, a substituted or unsubstituted $C_2$-$C_{60}$ heteroarylene group, a substituted or unsubstituted divalent non-aromatic condensed polycyclic group, or a substituted or unsubstituted divalent non-aromatic condensed heteropolycyclic group.

For example, $L_1$ and $L_2$ in Formula 1 may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthrenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a benzooxazolylene group, a dibenzofuranylene group, a dibenzothiophenylene group, and a benzocarbazolylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pyrrolylene group, an imidazolylene group, a pyrazolylene group, a pyridinylene group, a pyrazinylene group, a pyrimidinylene group, a pyridazinylene group, an isoindolylene group, an indolylene group, an indazolylene group, a purinylene group, a quinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a furanylene group, a benzofuranylene group, a thiophenylene group, a benzothiophenylene group, a thiazolylene group, an isothiazolylene group, a benzothiazolylene group, an isoxazolylene group, an oxazolylene group, a triazolylene group, a tetrazolylene group, an oxadiazolylene group, a triazinylene group, a benzooxazolylene group, a dibenzofuranylene group, a dibenzothiophenylene group, and a benzocarbazolylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{20}$ heteroaryl group.

In some embodiments, $L_1$ and $L_2$ in Formula 1 may be each independently selected from:

a phenylene group, a naphthylene group, a fluorenylene group, a spiro-fluorenylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, an isoindolylene group, an indolylene group, a quinolinylene group, a benzoquinolinylene group, a quinoxalinylene group, a quinazolinylene group, a cinnolinylene group, a carbazolylene group, and a triazinylene group; and a phenylene group, a naphthylene group, a fluorenylene group, a spiro-fluorenylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, an isoindolylene group, an indolylene group, a quinolinylene group, a benzoquinolinylene group, a quinoxalinylene group, a quinazolinylene group, a cinnolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group; a pyridazinyl group, an isoindolyl group, an indolyl group, a quinolinyl group, a benzoquinolinyl group, a quinoxalinyl group, a quinazolinyl group, a cinnolinylene group, a carbazolyl group, and a triazinyl group, but they are not limited thereto.

In some embodiments, $L_1$ and $L_2$ in Formula 1 may be each independently selected from:

a phenylene group, a naphthylene group, and a fluorenylene group; and a phenylene group, a naphthylene group, and a fluorenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, but they are not limited thereto.

a and b in Formula 1 may be each independently an integer selected from 0 to 5, for example, an integer selected from 0 to 3. In some embodiments, a and b in, Formula 1 may be each independently 0 or 1.

In Formula 1, when a is 0, -$(L_1)_a$- is a single bond, and when b is 0, -$(L_2)_b$- is a single bond. When a is 2 or more, a plurality of $L_1$ may be identical or different; and when b is 2 or more, a plurality of $L_2$ may be identical or different.

Ar₁ and Ar₂ in Formula 1 may be each independently a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted heteroaryl group, a substituted or unsubstituted monovalent non-aromatic condensed polycyclic group, or a substituted or unsubstituted monovalent non-aromatic condensed heteropolycyclic group.

For example, Ar₁ and Ar₂ in Formula 1 may be each independently selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, and a benzocarbazolyl group; and a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a benzooxazolyl group, a dibenzofuranyl group, a dibenzothiophenyl group, and a benzocarbazolyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_6$-$C_{20}$ aryl group, and a $C_2$-$C_{20}$ heteroaryl group.

In some embodiments, Ar₁ and Ar₂ in Formula 1 may be each independently selected from:

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, but there are not limited thereto.

In some embodiments, Ar₁ and Ar₂ in Formula 1 may be each independently represented by one of Formulae 3-1 to 3-20 below:

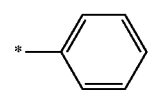

Formula 3-1

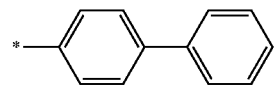

Formula 3-2

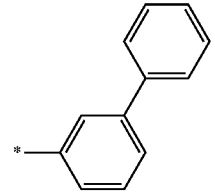

Formula 3-3

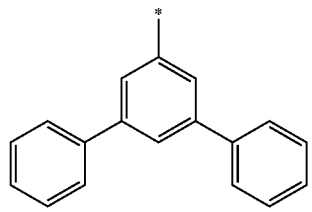

Formula 3-4

-continued

Formula 3-5

Formula 3-6

Formula 3-7

Formula 3-8

Formula 3-9

Formula 3-10

Formula 3-11

Formula 3-12

Formula 3-13

Formula 3-14

Formula 3-15

Formula 3-16

Formula 3-17

Formula 3-18

Formula 3-19

Formula 3-20 in Formulae 3-1 to 3-20, * indicates a binding site to "N", $L_1$, or $L_2$ of Formula 1.

$R_1$ to $R_4$, and $R_{11}$ to $R_{21}$ in Formula 1 are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ heteroaryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group;

a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_2$-$C_{60}$ heteroaryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a $C_6$-$C_{60}$ aryloxy group, a $C_6$-$C_{60}$ arylthio group, a monovalent non-aromatic condensed polycyclic group, and a monovalent non-aromatic condensed heteropolycyclic group; and —N($Q_{11}$)($Q_{12}$), —Si($Q_{13}$)($Q_{14}$)($Q_{15}$), and —B($Q_{16}$)($Q_{17}$) (where $Q_{11}$ to $Q_{17}$ may be each independently a $C_1$-$C_{60}$ alkyl group, a $C_1$-$C_{60}$ alkoxy group, a $C_6$-$C_{60}$ aryl group, a $C_2$-$C_{60}$ heteroaryl group, a $C_6$-$C_{60}$ aryloxy group, a $C_6$-$C_{60}$ arylthio group, a monovalent non-aromatic condensed polycyclic group, or a monovalent non-aromatic condensed heteropolycyclic group).

In some embodiments, in Formula 1, $R_1$ and $R_2$ may be each independently selected from:

a $C_1$-$C_{20}$ alkyl group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group.

In some embodiments, $R_1$ and $R_2$ in Formula 1 are each independently selected from a methyl group, an ethyl group, a propyl group, a butyl group, a pentyl group, a hexyl group, a heptyl group, and the groups represented by Formulae 3-1 to 3-20 (where * indicates a binding site to the C-9 carbon of fluorene of Formula 1), but are not limited thereto.

In some embodiments, $R_1$ and $R_2$ in Formula 1 may be each independently a phenyl group or a naphthyl group, but are not limited thereto.

$R_1$ and $R_2$ in Formula 1 may be identical or different. For example, $R_1$ and $R_2$ in Formula 1 may each be identical.

$R_3$, $R_4$, and $R_{11}$ to $R_{21}$ in Formula 1 are each independently selected from:

a hydrogen atom, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group.

In some embodiments, $R_3$, $R_4$, and $R_{11}$ to $R_{21}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group.

In some embodiments, $R_3$, $R_4$, and $R_{11}$ to $R_{21}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a propyl group, a butyl group, a pentyl group, a hexyl group, a heptyl group, and the groups represented by Formulae 3-1 to 3-20, but are not limited thereto.

In some embodiments, the amine-based compound represented by Formula 1 may contain at least one naphthalene ring in its molecular structure.

The expression "(Formula 1 or 1A) includes at least one naphthalene" used herein refers to a case that in the molecular structure of the amine-based compound represented by Formula 1 or 1A, at least one naphthalene necessarily exists regardless of where the naphthalene is present. For example, in the molecular structure of the amine-based compound represented by Formula 1 or 1A, the at least one naphthalene may be present as a terminal group (for example, see Compounds 1 to 3 to be explained later), or as a linking group (for example, see Compounds 4 and 5 to be explained later). Also, in the molecular structure of the amine-based compound represented by Formula 1 or 1A, the at least one naphthalene may be present where $Ar_2$ is located (for example, see Compounds 1, 2, 4, and 5 to be explained later), or where $Ar_1$ is located (for example, see Compound 3 to be explained later).

The amine-based compound described above may be represented by Formula 1A below:

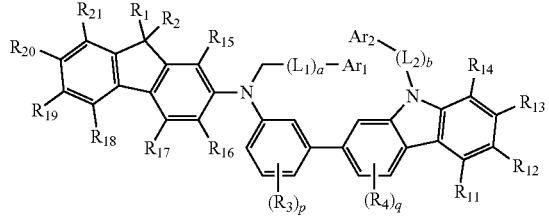

Formula 1A $L_1$, $L_2$, a, b, $Ar_1$, $Ar_2$, $R_1$ to $R_4$, $R_{11}$ to $R_{21}$, and p and q in Formula 1A are the same as already described in detail above with respect to Formula 1.

For example, in Formula 1A, $L_1$ and $L_2$ may be each independently selected from:

a phenylene group, a naphthylene group, a fluorenylene group, a spiro-fluorenylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, an isoindolylene group, an indolylene group, a quinolinylene group, a benzoquinolinylene group, a quinoxalinylene group, a quinazolinylene group, a cinnolinylene group, a carbazolylene group, and a triazinylene group; and a phenylene group, a naphthylene group, a fluorenylene group, a spiro-fluorenylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, an isoindolylene group, an indolylene group, a quinolinylene group, a benzoquinolinylene group, a quinoxalinylene group, a quinazolinylene group, a cinnolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a and b are each independently 0 or 1;

Ar₁ and Ar₂ may be each independently selected from:

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

$R_1$ and $R_2$ may be each independently selected from:

a $C_1$-$C_{20}$ alkyl group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

$R_3$, $R_4$, and $R_{11}$ to $R_{21}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group;

p and q may be each independently 0, 1, or 2; and

Formula 1 may include at least one naphthalene.

For example, at least one selected from $Ar_1$, $Ar_2$, $R_1$ to $R_4$ and $R_{11}$ to $R_{21}$ in Formula 1 may be selected from:

a naphthyl group;

a naphthyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, an anthracenyl group, and a fluorenyl group, each substituted with at least one naphthyl group.

In some embodiments, in Formula 1, $L_1$ and $L_2$ may be each independently selected from:

a phenylene group, a naphthylene group, and a fluorenylene group; and a phenylene group, a naphthylene group, and a fluorenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a and b are each independently 0 or 1;

$Ar_1$ and $Ar_2$ may be each independently selected from the groups represented by Formulae 3-1 to 3-20;

$R_1$ and $R_2$ may be each independently selected from a methyl group, an ethyl group, a propyl group, a butyl group, a pentyl group, a hexyl group, a heptyl group, and the groups represented by Formulae 3-1 to 3-20;

$R_3$, $R_4$, and $R_{11}$ to $R_{21}$ in Formula 1 may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a propyl group, a butyl group, a pentyl group, a hexyl group, a heptyl group, and the groups represented by Formulae 3-1 to 3-20; and p and q may be each independently 0, 1, or 2, but they are not limited thereto.

For example, at least one selected from $Ar_1$, $Ar_2$, $R_1$ to $R_4$, and $R_{11}$ to $R_{21}$ in Formula 1 or 1A may be one of Formulae 3-5 to 3-11 and 3-14 to 3-19.

The amine-based compound may be one of Compounds 1 to 7 illustrated below, but is not limited thereto:

1

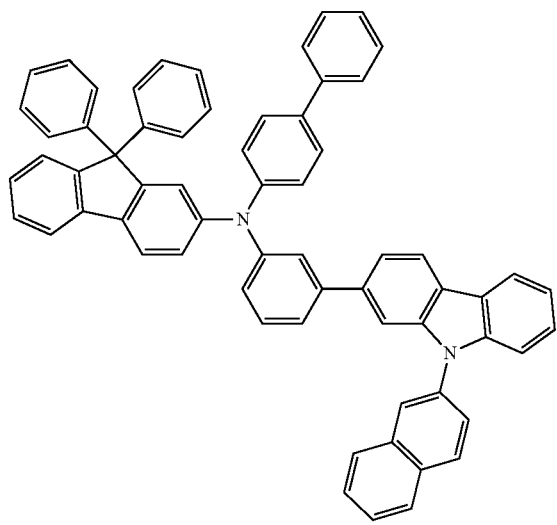

2

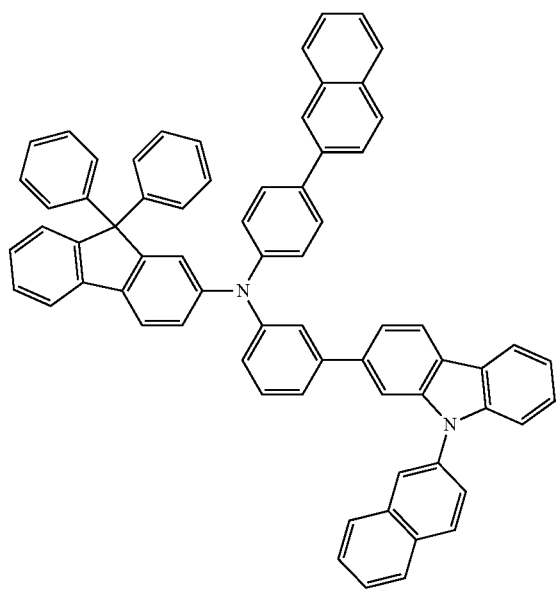

3

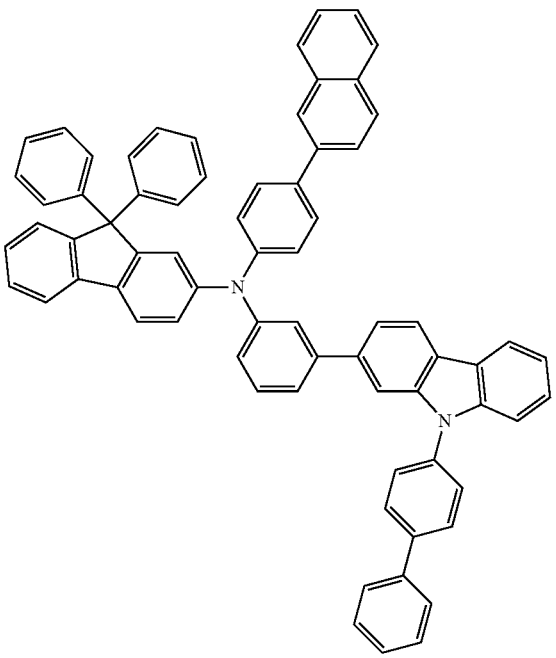

4

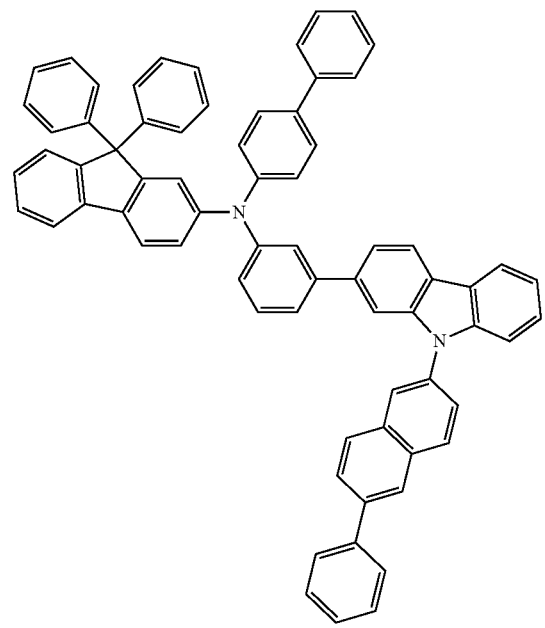

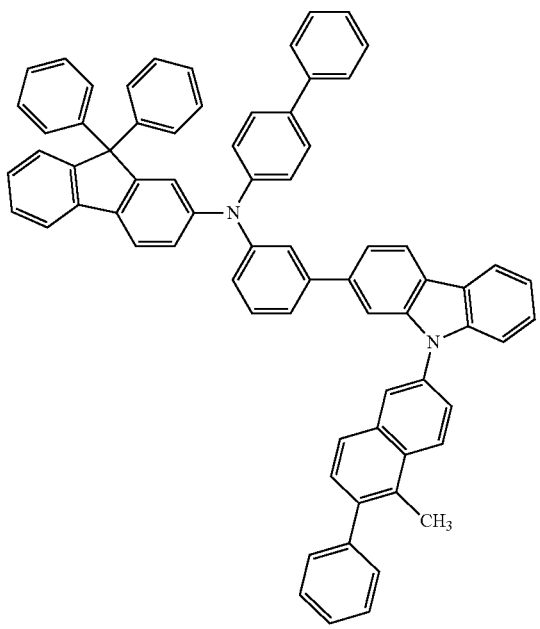

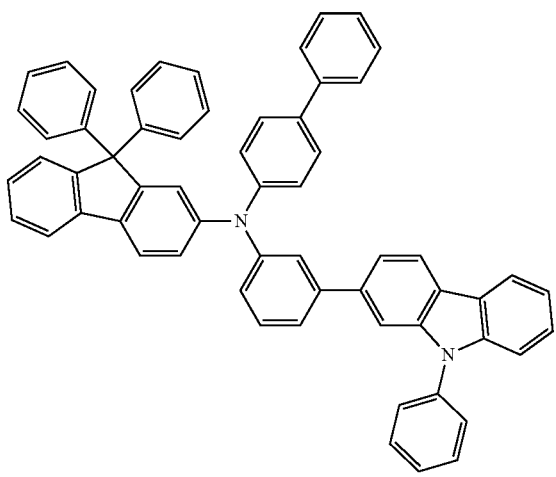

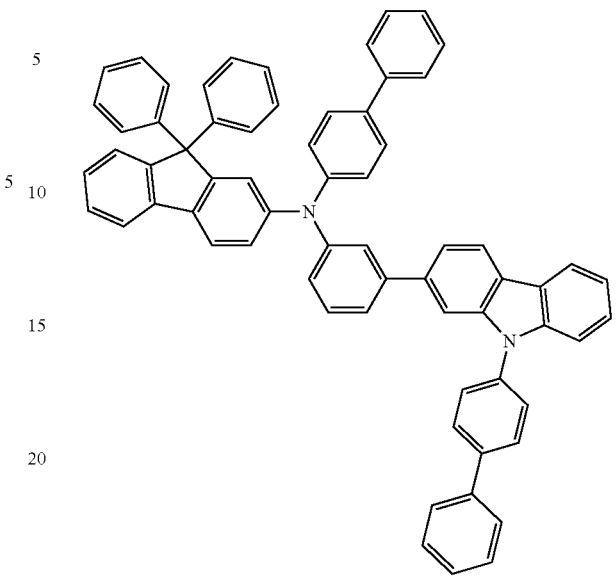

Formula 1 has, as a linking group between "carbazole" and "N", phen-1,3-ylene (i.e., 1,3-phenylene) that is substituted or unsubstituted with at least one $R_3$ (see Formula 1' below). Due to the inclusion of phen-1,3-ylene, the amine-based compound represented by Formula 1 has a high lowest unoccupied molecular orbital (LUMO) energy level and a large energy band gap. Accordingly, when the amine-based compound represented by Formula 1 is used (utilized) in a hole transport region, the flow of electrons from an emission layer to the hole transport region is reduced or prevented, thereby enabling the production of an organic light-emitting device having high luminescent efficiency.

Formula 1' phen-1,3-ylene

Since the amine-based compound represented by Formula 1 has a fluorene ring, a high hole mobility may be obtained. Accordingly, even when a layer having the amine-based compound is formed as a thick film between an anode and a cathode, the driving voltage of an organic light-emitting device may not substantially increase.

Thus, an organic light-emitting device using (utilizing) the amine-based compound represented by Formula 1 may have high efficiency, high brightness, and long lifespan.

The amine-based compound represented by Formula 1 may be synthesized by using (utilizing) a suitable organic synthesis method. A synthesis method of the amine-based compound should be apparent to one of ordinary skill in the art in view of the following embodiments.

The amine-based compound of Formula 1 may be used (utilized) between a pair of electrodes of an organic light-emitting device. For example, the amine-based compound may be used (utilized) in at least one selected from a hole injection layer, a hole transport layer, and a functional layer having a hole injection capability, and a hole transport capability.

Accordingly, an organic light-emitting device according to an embodiment includes: a first electrode; a second electrode facing the first electrode; and an organic layer that is disposed between the first electrode and the second electrode and includes an emission layer, wherein the organic layer includes at least one of the amine-based compounds described above.

The expression "(an organic layer) includes at least one amine-based compounds" used herein may include a case in which "(an organic layer) includes one amine-based compound of Formula 1, and a case in which two or more different amine-based compounds of Formula 1 are included.

For example, the organic layer may include, as the amine-based compound, only Compound 1. In this regard, Compound 1 may exist in a hole transport layer of the organic light-emitting device. In other embodiments, the organic layer may include, as the amine-based compound, Compound 1 and Compound 2. In this regard, Compound 1 and Compound 2 may exist in an identical layer (for example, Compound 1 and Compound 2 may both exist in a hole transport layer), or different layers (for example, Compound 1 may exist in a hole transport layer and Compound 2 may exist in an emission layer).

The organic layer includes i) a hole transport region that is disposed between the first electrode and the emission layer, and includes at least one selected from a hole injection layer, a hole transport layer, a functional layer having a hole injection capability and a hole transport capability, a buffer layer, and an electron blocking layer; and ii) an electron transport region that is disposed between the emission layer and the second electrode, and includes at least one selected from a hole blocking layer, an electron transport layer, and an electron injection layer. In this regard, the hole transport region may include the amine-based compound. The hole transport region may further include a p-dopant. In some embodiments, the hole transport region includes a hole transport layer, which includes the amine-based compound.

The term "organic layer" used herein refers to a single layer and/or a plurality of layers disposed between the first electrode and the second electrode of an organic light-emitting device.

The drawing is a schematic view of an organic light-emitting device 10 according to an embodiment. Hereinafter, the structure of an organic light-emitting device according to an embodiment and a method of manufacturing an organic light-emitting device according to an embodiment will be described in connection with the drawing.

For use (usage) as the substrate 11, any suitable substrate that is used (utilized) in general organic light-emitting devices may be used (utilized), and the substrate 11 may be a glass substrate or a transparent plastic substrate, each with excellent mechanical strength, thermal stability, transparency, surface smoothness, ease of handling, and water-resistance.

The first electrode 13 may be formed by, for example, depositing or sputtering a material for the first electrode on the substrate 11. When the first electrode 13 is an anode, the material for the first electrode 110 may be selected from materials with a high work function to allow holes to enter easily. The first electrode 13 may be a reflective electrode or a transmissive electrode. The material for the first electrode 120 may be a transparent and highly conductive material, and examples of such a material are indium tin oxide (ITO), indium zinc oxide (IZO), tin oxide ($SnO_2$), and zinc oxide (ZnO). In some embodiments, when magnesium (Mg), aluminum (Al), aluminum-lithium (Al—Li), calcium (Ca), magnesium-indium (Mg—In), or magnesium-silver (Mg—Ag) is used (utilized), the first electrode 13 may be formed as a reflective electrode.

The first electrode 13 may have a single-layer structure, or a multi-layer structure including two or more layers. For example, the first electrode 13 may have a three-layered structure of ITO/Ag/ITO, but the structure of the first electrode 110 is not limited thereto.

The organic layer 15 is disposed on the first electrode 13.

The organic layer 15 may include a hole injection layer, a hole transport layer, a buffer layer, an emission layer, an electron transport layer, and an electron injection layer.

A hole injection layer (HIL) may be formed on the first electrode 13 by using (utilizing) various suitable methods, such as vacuum deposition, spin coating, casting, langmuir-blodgett (LB) deposition, or the like.

When the hole injection layer is formed by vacuum deposition, the deposition conditions may vary according to the material that is used (utilized) to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the hole injection layer is formed using (utilizing) spin coating, coating conditions may vary according to the material used (utilized) to form the hole injection layer, and the structure and thermal properties of the hole injection layer. For example, a coating speed may be from about 2000 rpm to about 5000 rpm, and a temperature at which a heat treatment is performed to remove a solvent after coating may be from about 80° C. to about 200° C. However, the coating conditions are not limited thereto.

For use (usage) as a hole injection material, any suitable hole injection material may be used (utilized), and examples of suitable hole injection materials are N,N'-diphenyl-N,N'-bis-[4-(phenyl-m-tolyl-amino)-phenyl]-biphenyl-4,4'-diamine (DNTPD), a phthalocyanine compound (such as copper phthalocyanine), 4,4',4''-tris(3-methylphenylphenylamino) triphenylamine (m-MTDATA), N,N'-di(1-naphthyl)-N,N'-diphenylbenzidine (NPB), TDATA, 2-TNATA, a polyaniline/dodecylbenzenesulfonic acid (pani/DBSA), poly(3,4-ethylenedioxythiophene)/poly(4-styrenesulfonate) (PEDOT/PSS), polyaniline/camphor sulfonicacid (pani/

CSA), and (polyaniline)/poly(4-styrenesulfonate) (PANI/PSS), but they are not limited thereto.

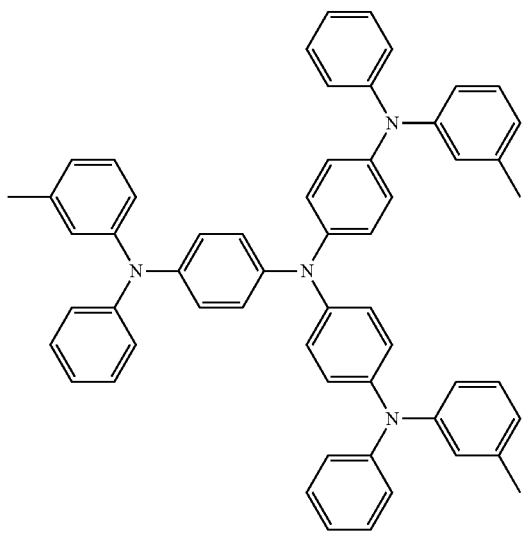

m-MTDATA

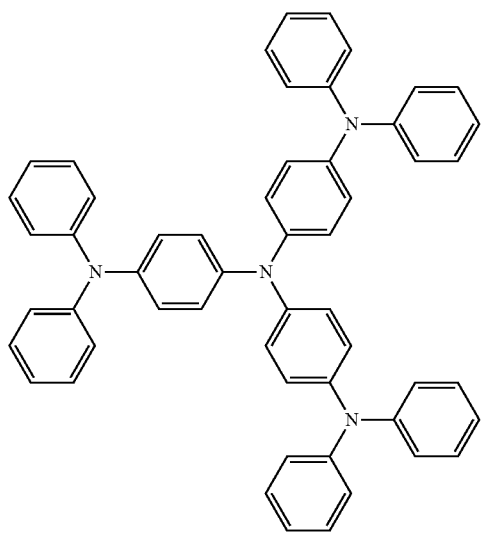

TDATA

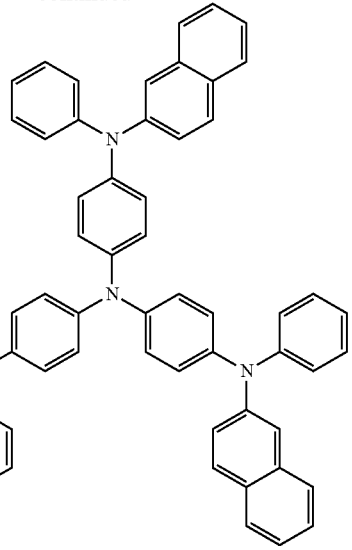

2-TNATA

In some embodiments, the hole injection layer may include the amine-based compound represented by Formula 1, but may instead include other materials.

A thickness of the hole injection layer may be in a range of about 100 Å to about 10,000 Å, for example, about 100 Å to about 1000 Å. In one embodiment, when the thickness of the hole injection layer is within the ranges described above, excellent electron injection characteristics are obtained without a substantial increase in driving voltage.

Then, a hole transport layer (HTL) may be formed on the hole injection layer by using (utilizing) vacuum deposition, spin coating, casting, or LB. When the hole transport layer is formed by vacuum deposition or spin coating, the deposition or coating conditions may be similar to those applied to form the hole injection layer although the deposition or coating conditions may vary according to the material that is used (utilized) to form the hole transport layer.

As a suitable hole transport material, the amine-based compound represented by Formula 1 may be used (utilized).

A thickness of the hole transport layer may be in a range of about 50 Å to about 2,000 Å, for example, about 100 Å to about 1,500 Å. In one embodiment, when the thickness of the hole transport layer is within these ranges, the hole transport layer has satisfactory hole transporting ability without a substantial increase in driving voltage.

In some embodiments, instead of the hole injection layer and the hole transport layer, a functional layer (hereinafter referred to as an H-functional layer) having a hole injection capability and a hole transport capability may include at least one material selected from the materials used (utilized) to form the hole injection layer and at least one material selected from the materials used (utilized) to form the hole transport layer, and a thickness of the H-functional layer may be in a range of about 100 Å to about 10000 Å, for example, about 100 Å to about 1000 Å. In one embodiment, when the thickness of the H-functional layer is within these ranges, satisfactory hole injection and transport characteristics are obtained without a substantial increase in driving voltage.

In some embodiments, the H-functional layer may include the amine-based compound represented by Formula 1, but may instead include other materials.

The hole transport region may include at least one selected from the hole injection layer, the hole transport layer, and the H-functional layer, and may further include a charge-generation material to increase the conductivity of a respective layer, in addition to such suitable hole injection materials, suitable hole transport materials, and/or suitable materials having both hole injection and hole transport capabilities.

The charge-generation material may be, for example, a p-dopant. The p-dopant may be one of a quinone derivative, a metal oxide, and a cyano group-containing compound, but is not limited thereto. Non-limiting examples of the p-dopant are a quinone derivative (such as tetracyanoquinonedimethane (TCNQ) or 2,3,5,6-tetrafluoro-tetracyano-1,4-benzoquinonedimethane (F4-TCNQ)); a metal oxide (such as tungsten oxide or molybdenium oxide); and a cyano group-containing compound (such as Compound 200 below), but are not limited thereto.

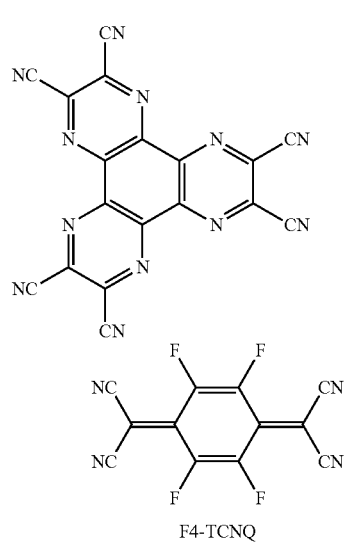

When the hole injection layer, the hole transport layer or the H-functional layer further includes a charge-generation material, the charge-generation material may be homogeneously dispersed or non-homogeneously distributed in the hole injection layer, the hole transport layer, or the H-functional layer.

A buffer layer may be disposed between the emission layer and at least one selected from the hole injection layer, the hole transport layer, and the H-functional layer. Also, the buffer layer may compensate for an optical resonance distance according to a wavelength of light emitted from the emission layer, and thus, efficiency of a formed organic light-emitting device may be improved. The buffer layer may include a suitable hole injection material and a hole transport material. Also, the buffer layer may include a material that is identical to one of the materials included in the hole injection layer, the hole transport layer, and the H-functional layer disposed under the buffer layer.

Subsequently, an emission layer (EML) may be formed on the hole transport layer, the H-functional layer, or the buffer layer by spin coating, casting, or an LB method. When the emission layer is formed by vacuum deposition or spin coating, the deposition and coating conditions may be similar to those for the formation of the hole injection layer, though the conditions for deposition and coating may vary according to the material that is used (utilized) to form the emission layer.

The emission layer may include a host and a dopant. The dopant may include at least one selected from a fluorescent dopant and a phosphorescent dopant. The phosphorescent dopant may be an organometallic compound including Ir, Pt, Os, Ti, Zr, Hf, Eu, Tb, or Tm.

When the organic light-emitting device is a full color organic light-emitting device, the emission layer may be patterned into a red emission layer, a green emission layer, and a blue emission layer. In some embodiments, the emission layer may have a stacked structure of two or more layers of a red emission layer, a green emission layer, and a blue emission layer, but is not limited thereto.

Also, at least one selected from the red emission layer, the green emission layer, and the blue emission layer may include the dopants described below (ppy=phenylpyridine).

For example, compounds illustrated below may be used (utilized) as a blue dopant, but the blue dopant is not limited thereto.

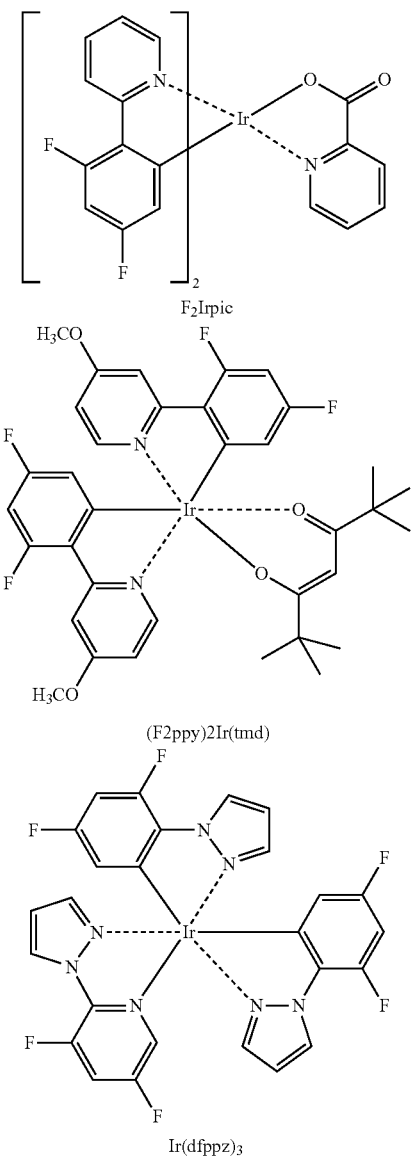

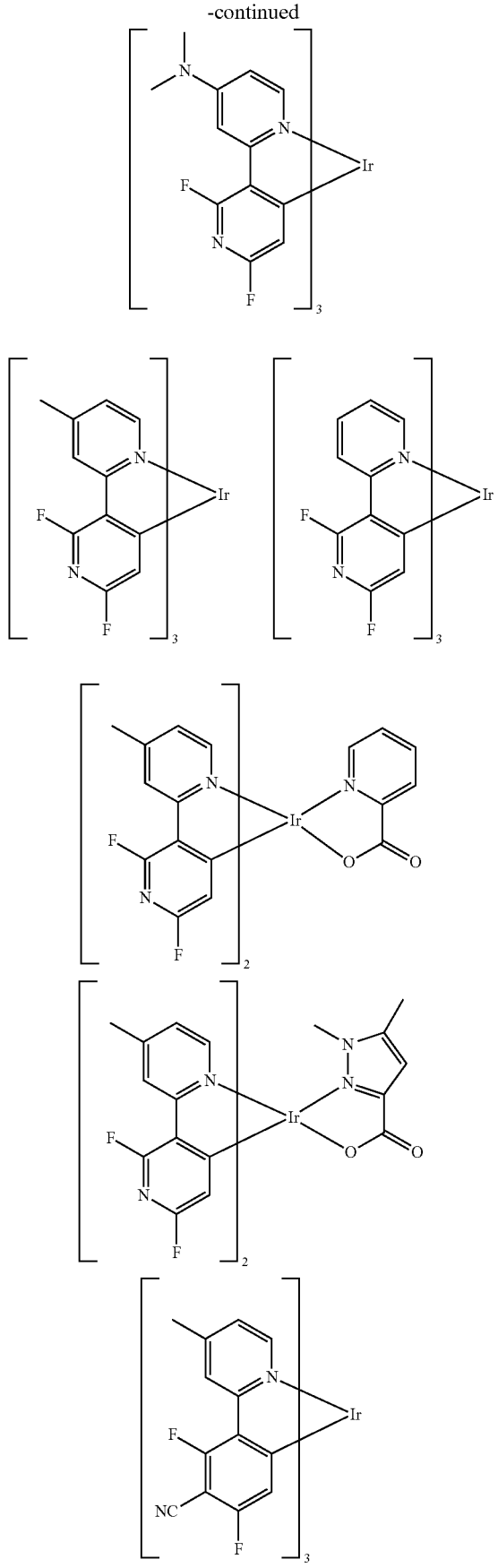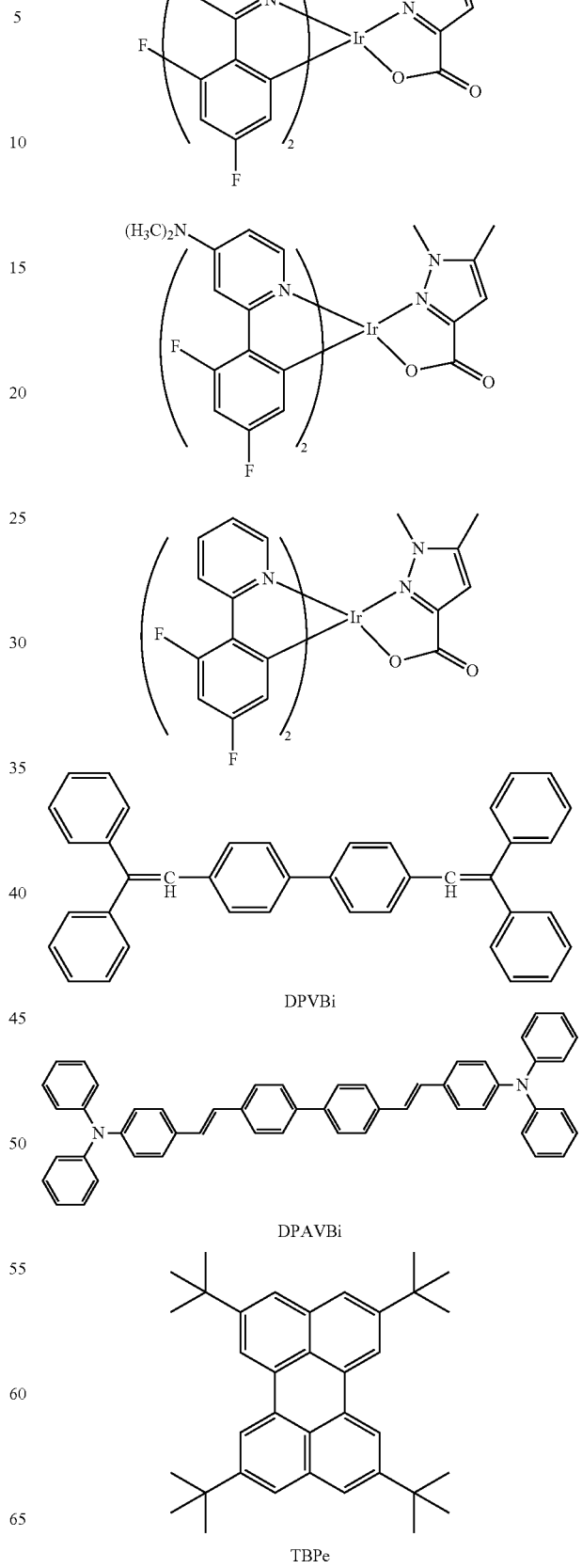
DPVBi
DPAVBi
TBPe

For example, compounds illustrated below may be used (utilized) as a red dopant, but the red dopant is not limited thereto. According to one embodiment, the red dopant may be DCM or DCJTB.
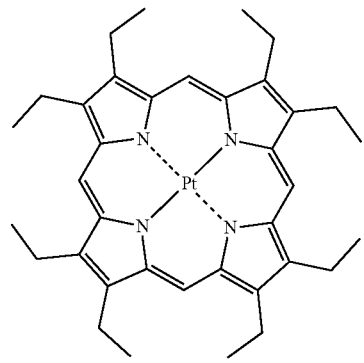
PtOEP
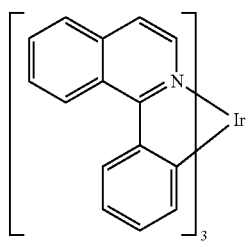
Ir(piq)₃
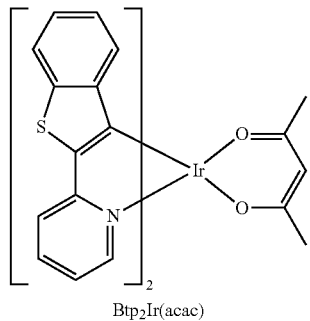
Btp₂Ir(acac)
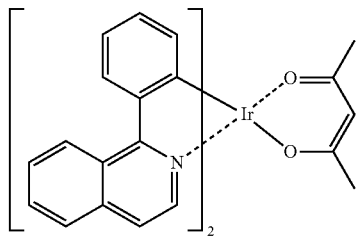
Ir(pq)₂(acac)
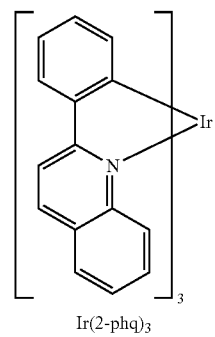
Ir(2-phq)₃
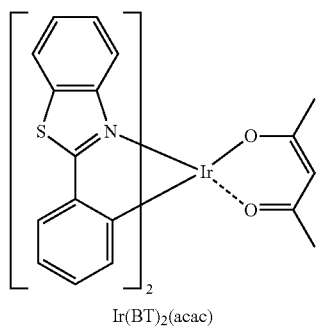
Ir(BT)₂(acac)
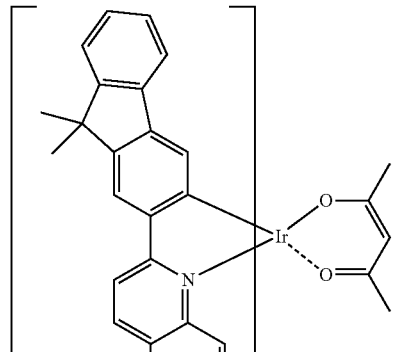
Ir(flq)₂(acac)
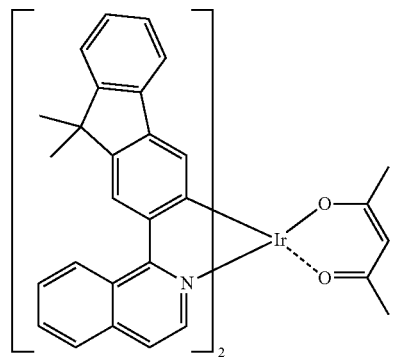
Ir(fliq)₂(acac)

-continued
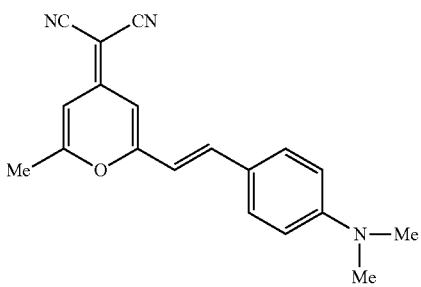
DCM
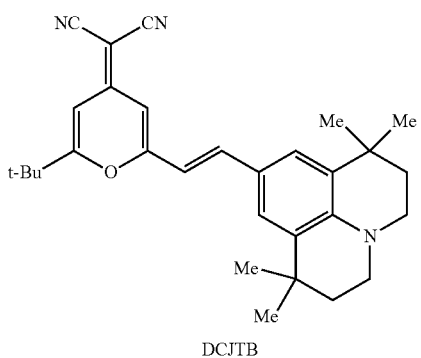
DCJTB
For example, compounds illustrated below may be used (utilized) as a green dopant, but the green dopant is not limited thereto. In some embodiments, the green dopant may be C545T.
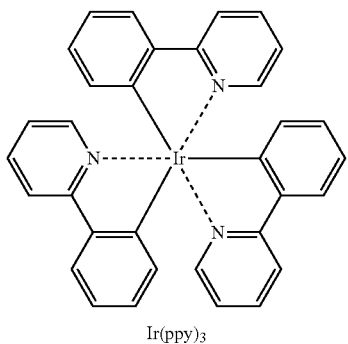
Ir(ppy)₃
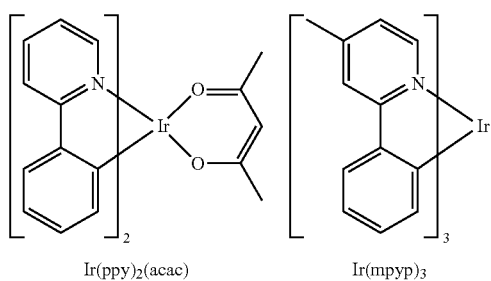
Ir(ppy)₂(acac)    Ir(mpyp)₃
-continued
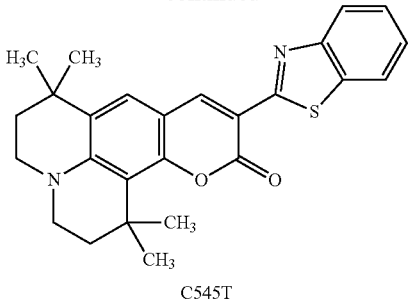
C545T
Also, the dopant available for use (usage) in the emission layer may be a complex described below, but is not limited thereto:
D1
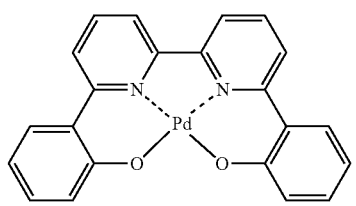
D2
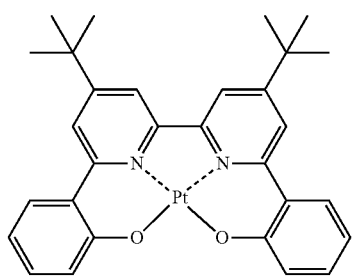
D3
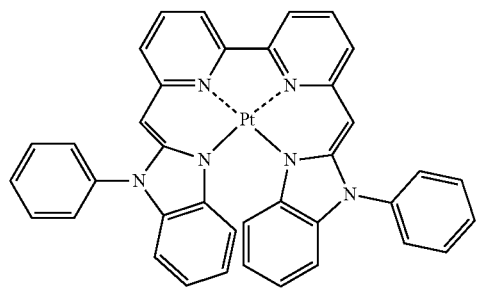
D4
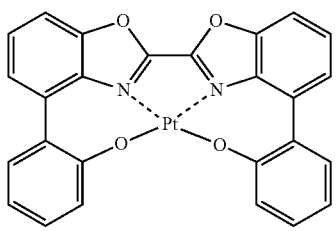

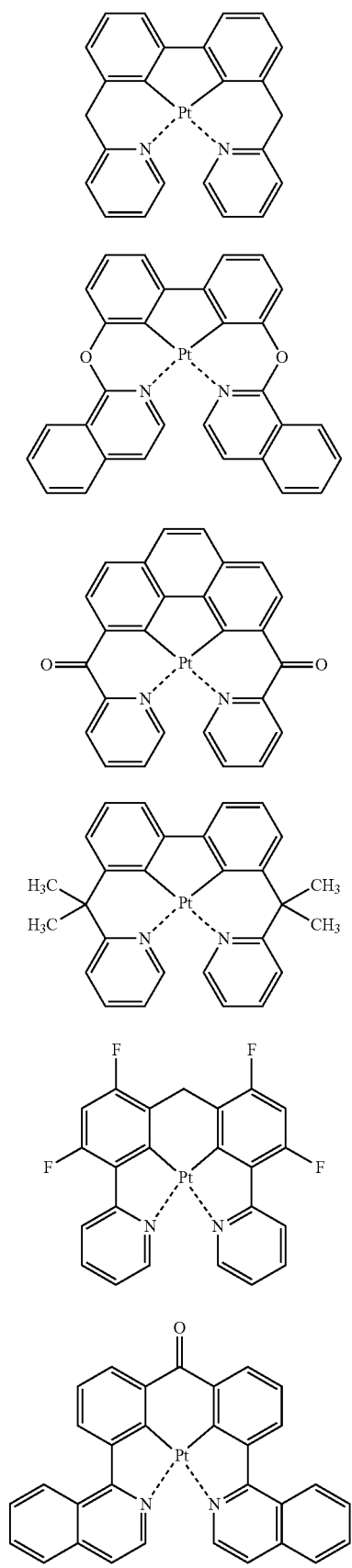
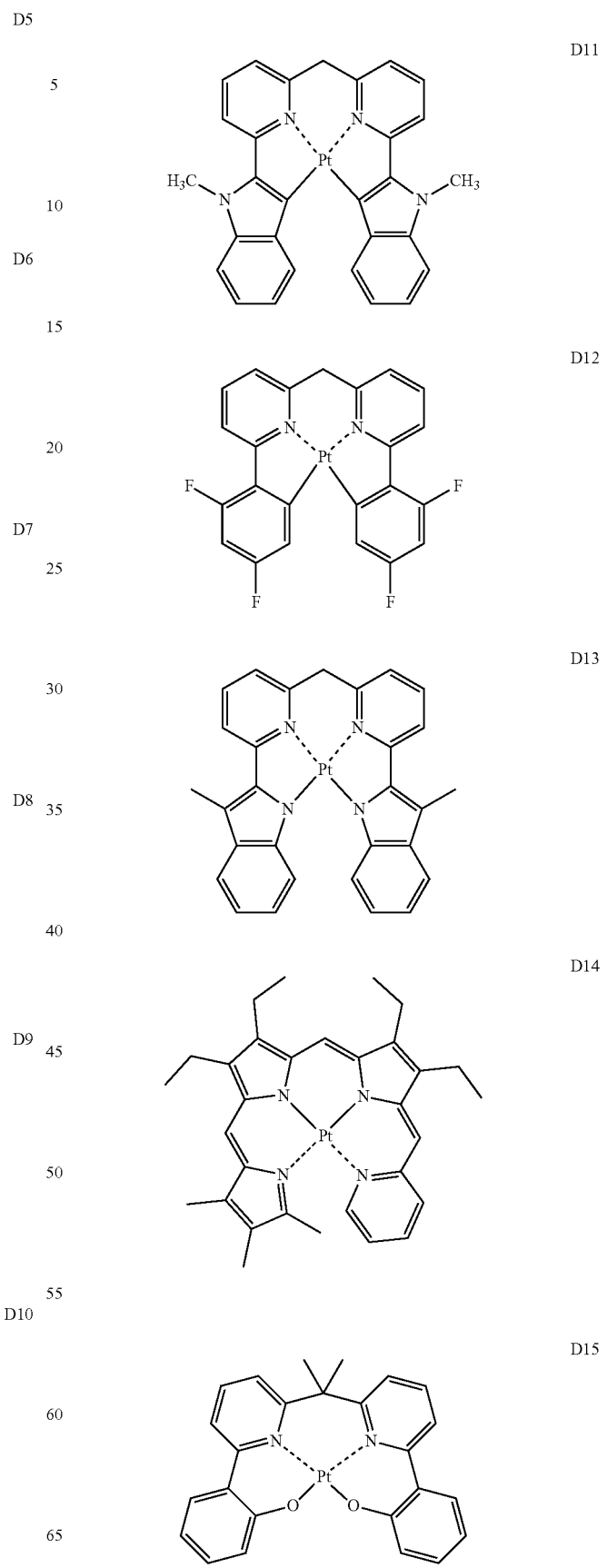

-continued
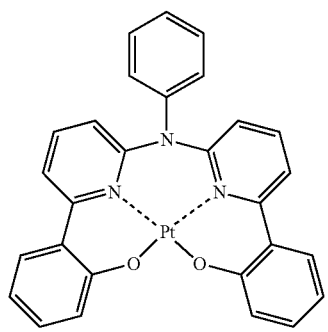
D16
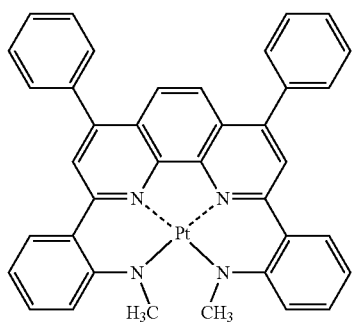
D17
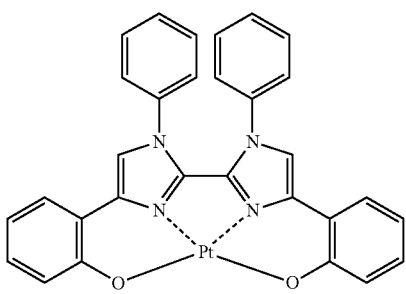
D18
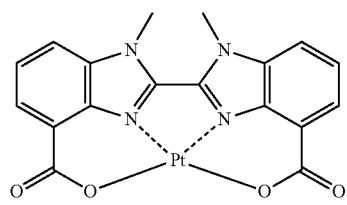
D19
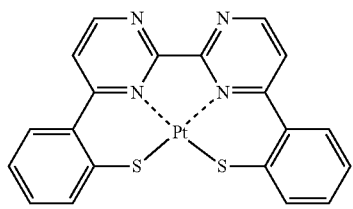
D20
-continued
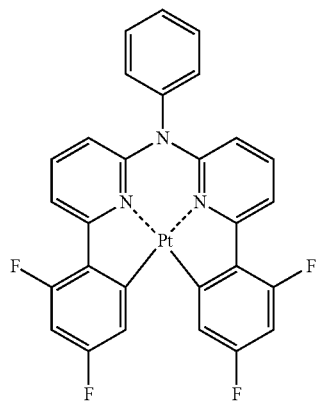
D21
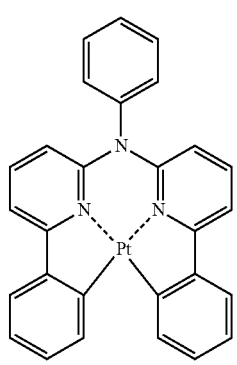
D22
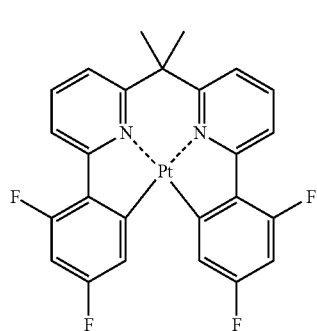
D23
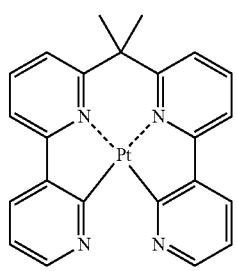
D24
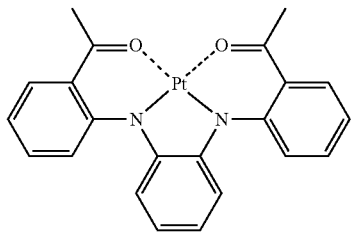
D25

D26 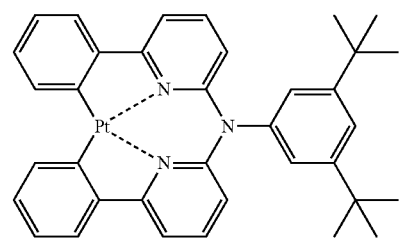
D27 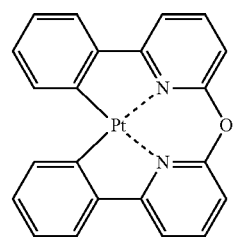
D28 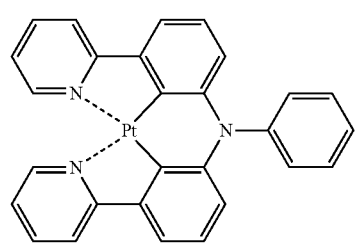
D29 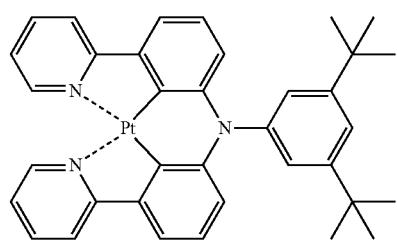
D30 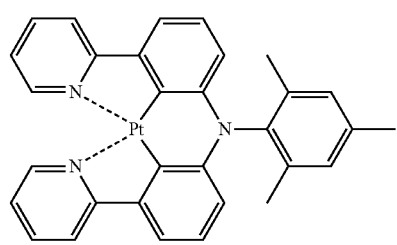
D31 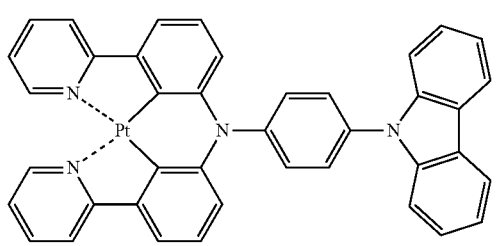
D32 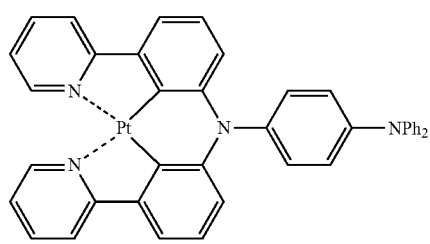
D33 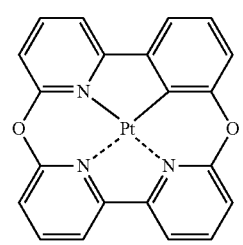
D34 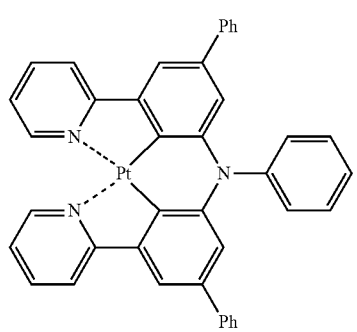
D35 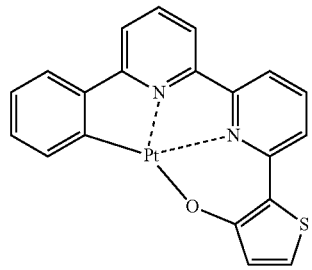
D36 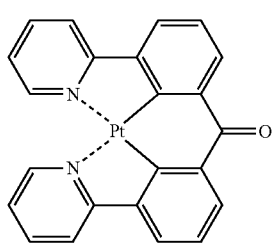

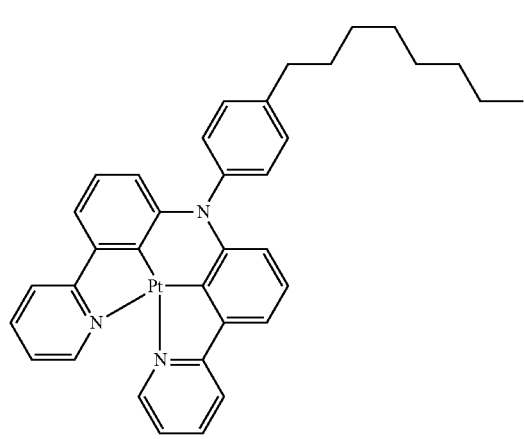
D37
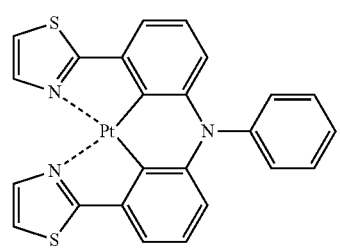
D38
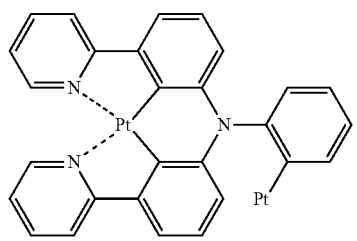
D39
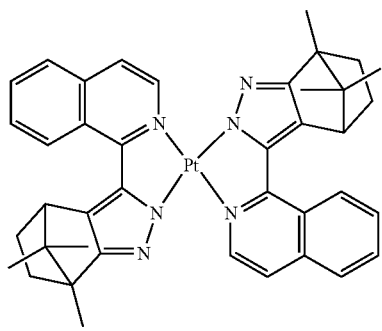
D40
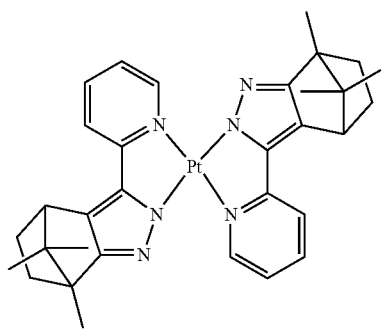
D41
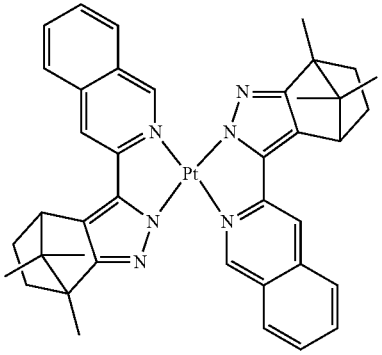
D42
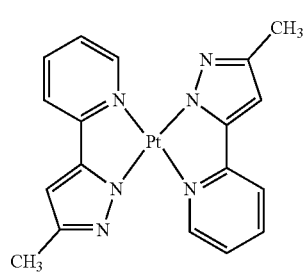
D43
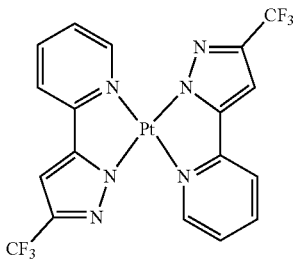
D44
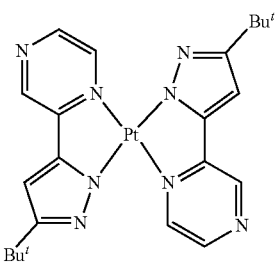
D45
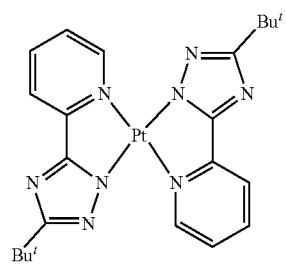
D46

-continued

D47
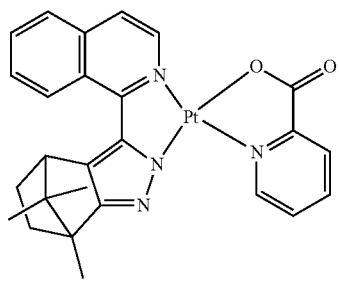

D48
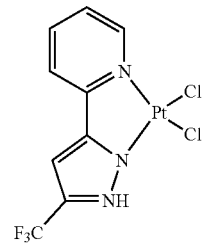

D49
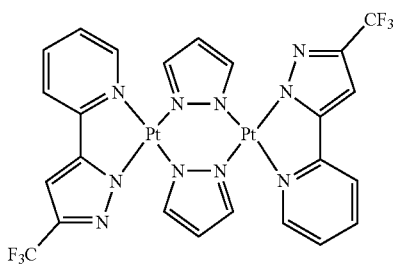

D50
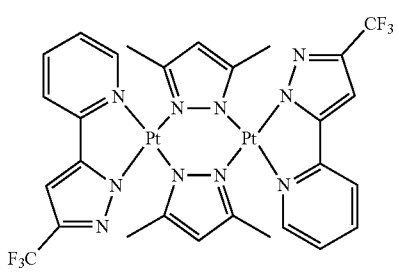

Also, the dopant available for use (usage) in the emission layer may be an Os-complex described below, but is not limited thereto:

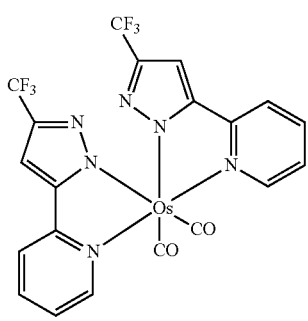

Os(fppz)₂(CO)₂

-continued

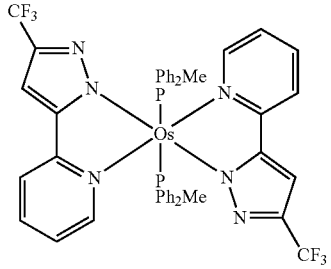

Os(fppz)₂(PPh₂Me)₂

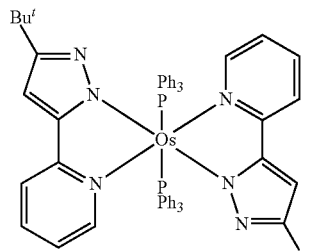

Os(bppz)₂(PPh₃)₂

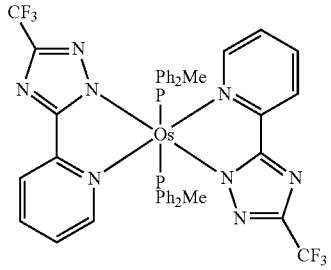

Os(fptz)₂(PPh₂Me)₂

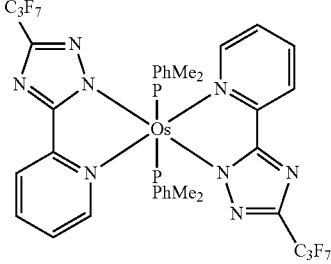

Os(hptz)₂(PPh₂Me₂)₂

For use (usage) as a host for the emission layer, at least one of any suitable hosts may be used (utilized). Examples of suitable hosts are Alq₃, 4,4'-N,N'-dicarbazole-biphenyl (CBP), PVK, 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), mCP, and OXD-7, but are not limited thereto.

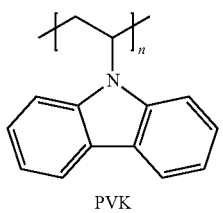

PVK

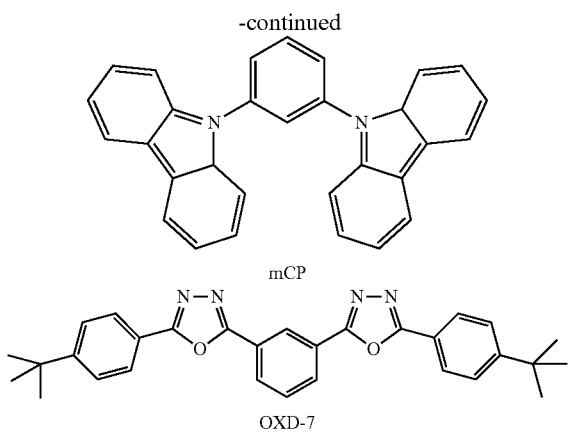

mCP

OXD-7

In some embodiments, a carbazole-based compound represented by Formula 10 may be used (utilized) as a host.

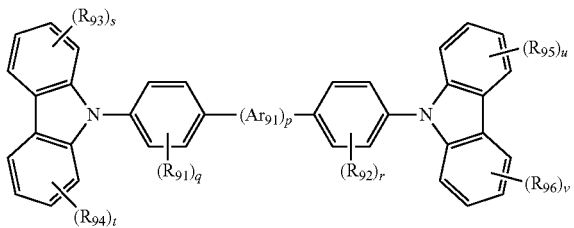

Formula 10 wherein in Formula 10, $Ar_{91}$ may be a substituted or unsubstituted $C_1$-$C_{60}$ alkylene group, a substituted or unsubstituted $C_2$-$C_{60}$ alkenylene group, —C(=O)—, —N($R_{100}$)— (where $R_{100}$ is a substituted or unsubstituted $C_6$-$C_{60}$ aryl group or a substituted or unsubstituted $C_2$-$C_{60}$ heteroaryl group), a substituted or unsubstituted $C_6$-$C_{60}$ arylene group, or a substituted or unsubstituted $C_2$-$C_{60}$ heteroarylene group;

p is an integer selected from 0 to 7;

$R_{91}$ to $R_{96}$ may be each independently a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted C3-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group, wherein two neighboring substituents selected from $R_{91}$ to $R_{96}$ may bind to each other to selectively form a substituted or unsubstituted $C_4$-$C_{20}$ alicyclic group, a substituted or unsubstituted $C_2$-$C_{20}$ hetero alicyclic group, a substituted or unsubstituted $C_6$-$C_{20}$ aromatic group, or a substituted or unsubstituted $C_2$-$C_{20}$ hetero aromatic group; and q, r, s, t, u and v may be each independently an integer selected from 1 to 4.

$Ar_{91}$ in Formula 10 may be a $C_1$-$C_5$ alkylene group, a $C_2$-$C_5$ alkenylene group, —C(=O)—, or —N($R_{100}$)—. $R_{100}$ may be selected from:

a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

$R_{91}$ to $R_{96}$ in Formula 10 may be each independently selected from:

a hydrogen atom, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof.

The carbazole-based compound may be one of the compounds H1 to H30 below, but is not limited thereto:

H1

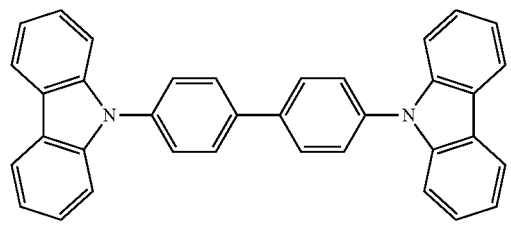

H2

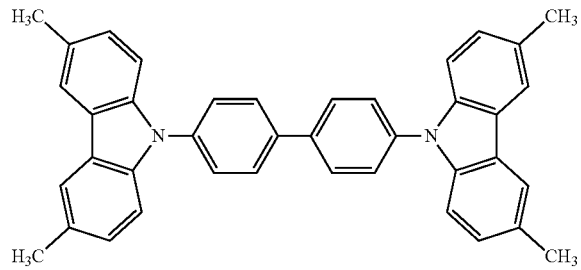

-continued
| | |
|---|---|
| H3 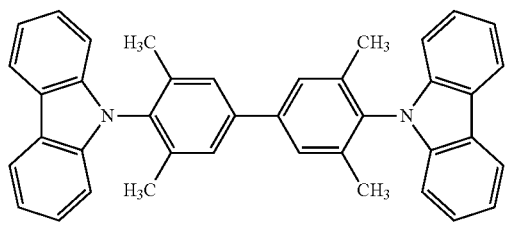 | H4 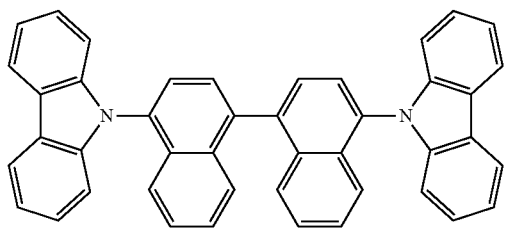 |
| H5 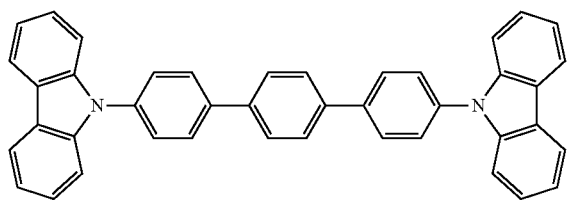 | H6 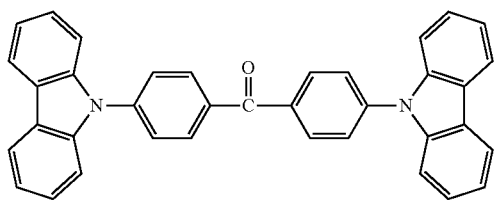 |
| H7 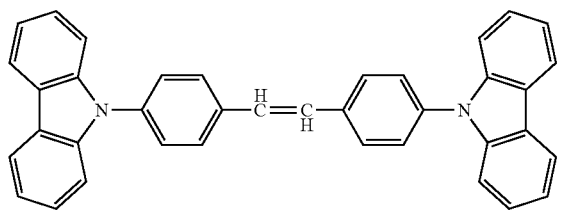 | H8 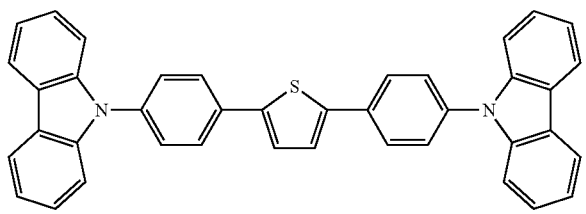 |
| H9 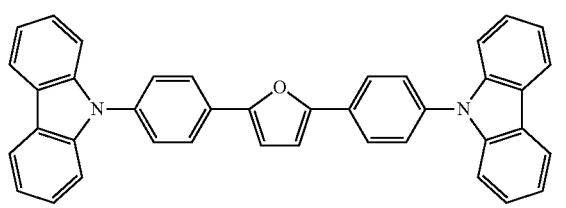 | H10 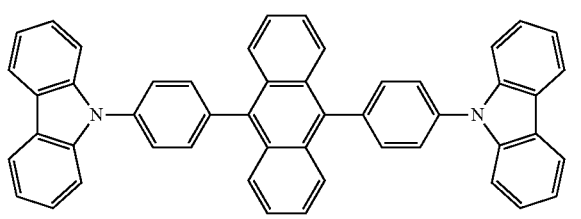 |
| H11 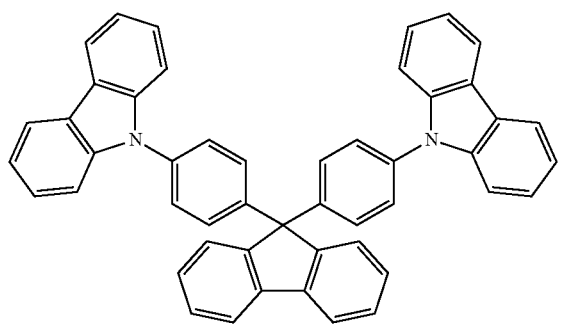 | H12 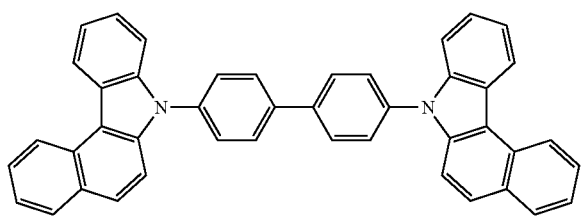 |

H13
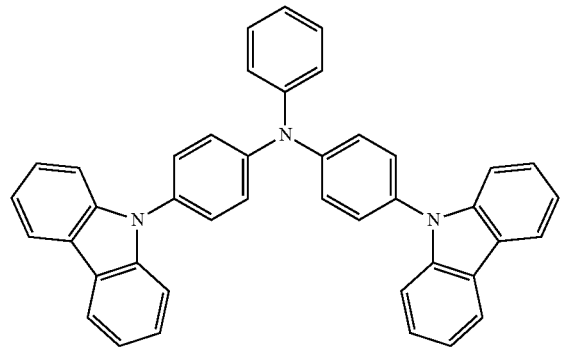
H14
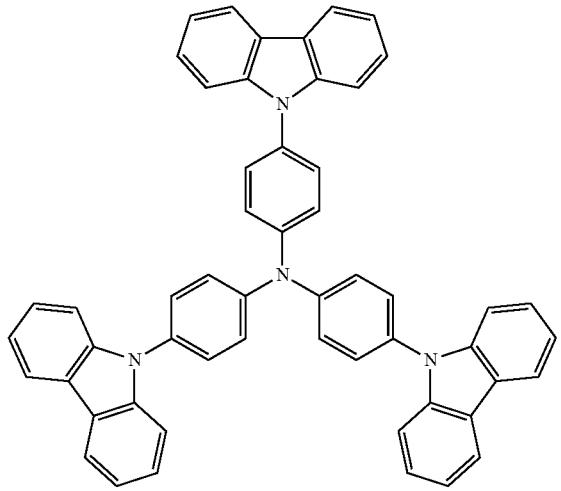
H15
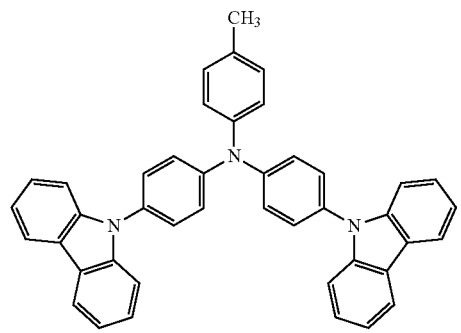
H16
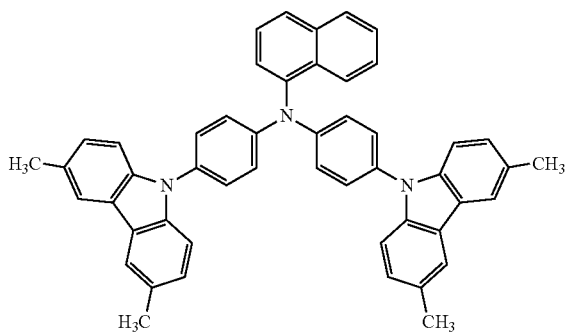
H17
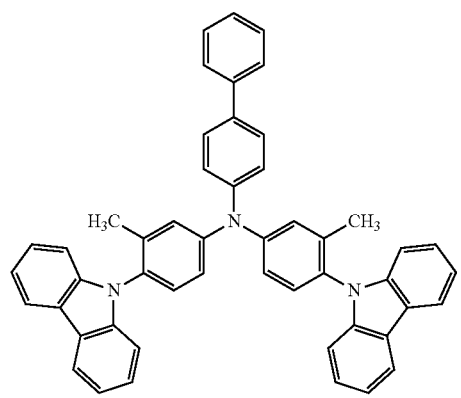
H18
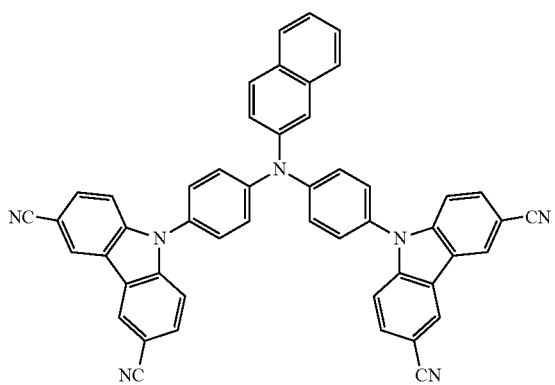

H19
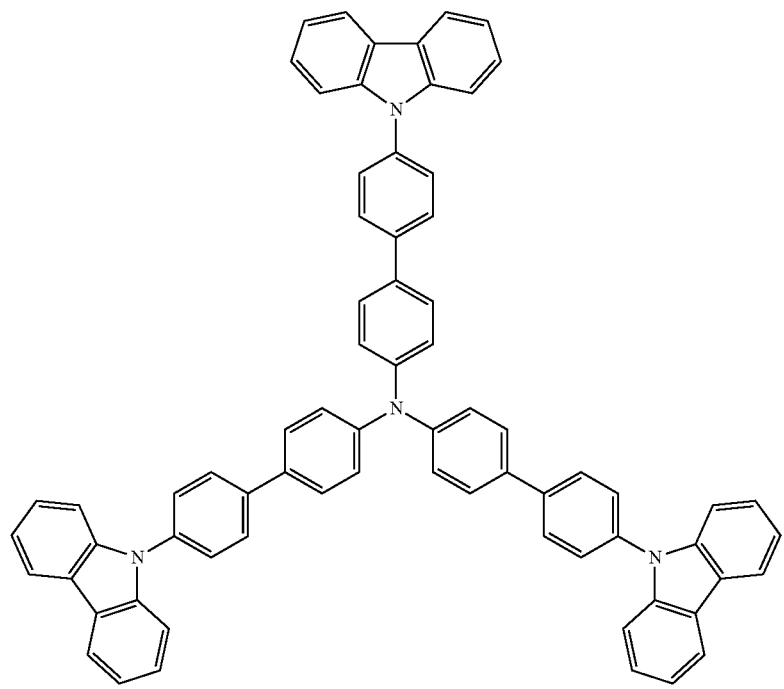
H20
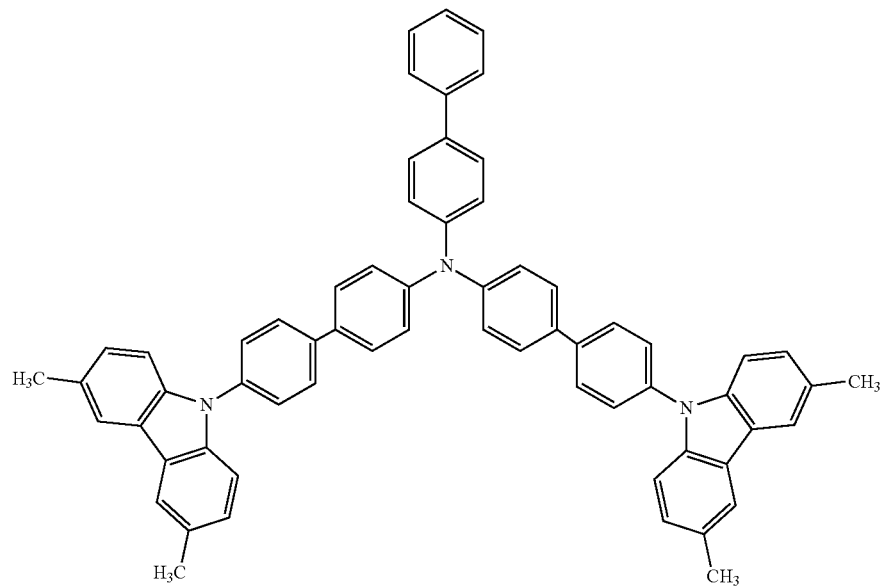

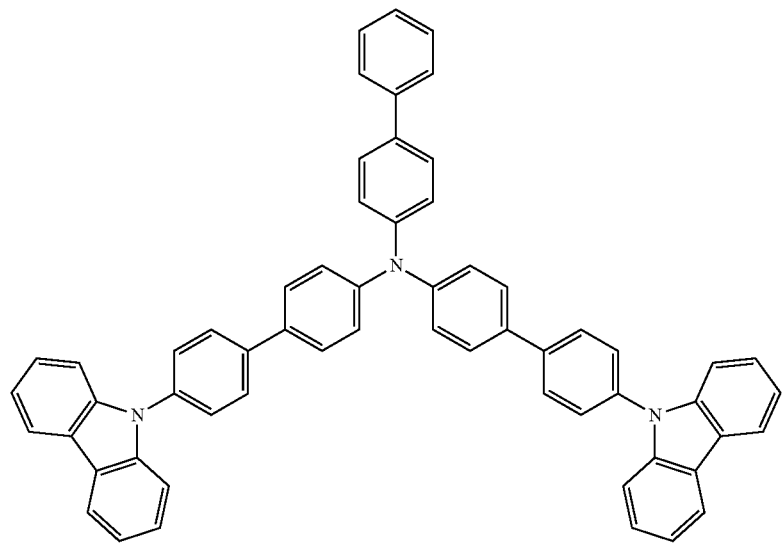
H21
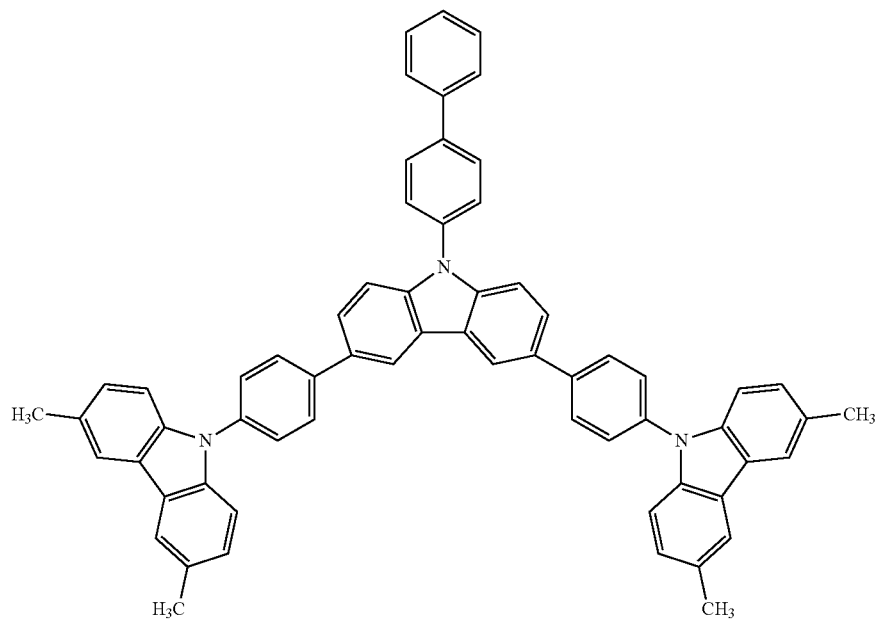
H22
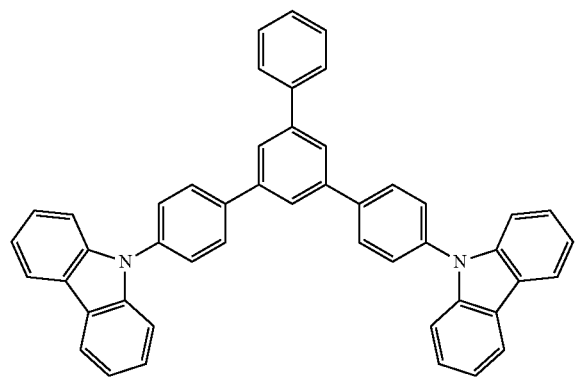
H23

-continued
H24
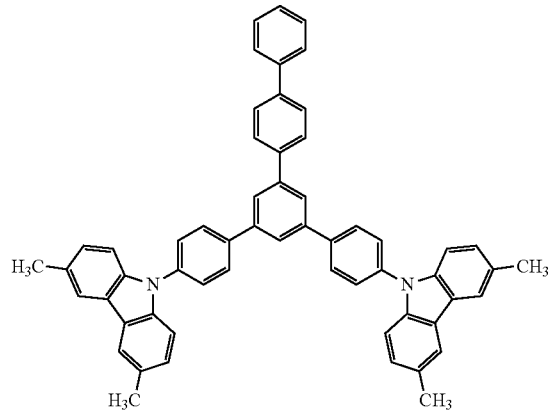
H25
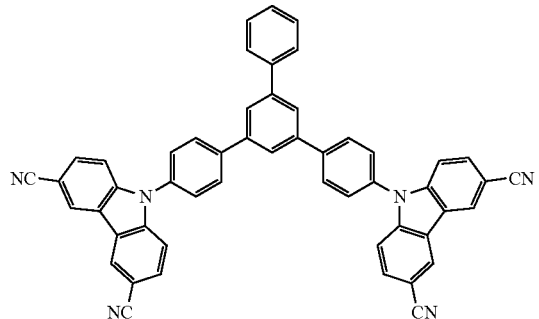
H26
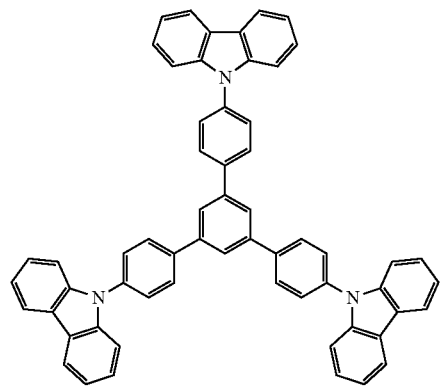
H27
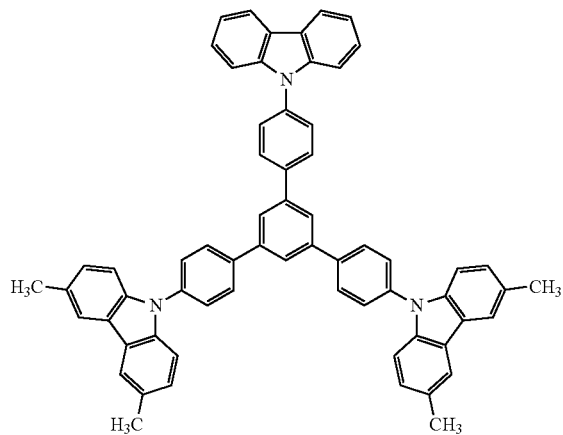
H28
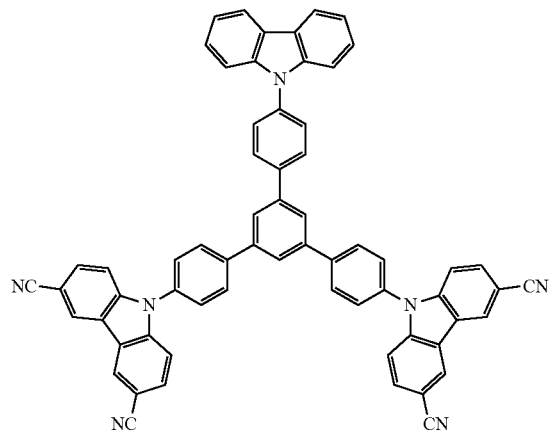
H29
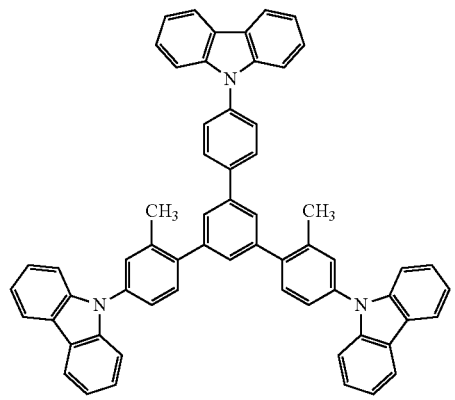

-continued

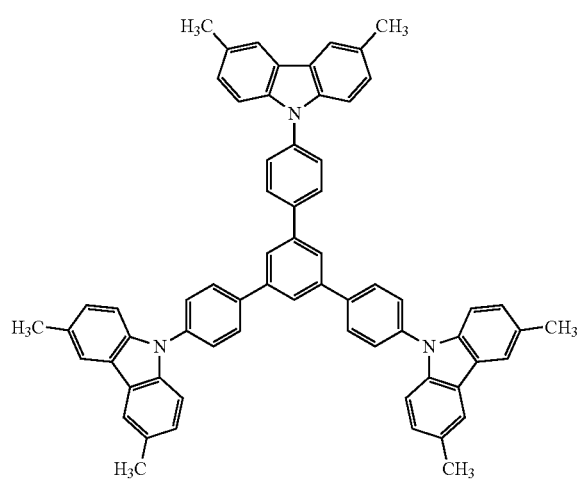

H30

When the emission layer includes a host and a dopant, an amount of the dopant may be in a range of about 0.01 to about 15 parts by weight based on 100 parts by weight of the host, but is not limited thereto.

A thickness of the emission layer may be in a range of about 100 Å to about 1,000 Å, for example, about 200 Å to about 600 Å. In one embodiment, when the thickness of the emission layer is within these ranges, excellent light-emission characteristics are obtained without a substantial increase in driving voltage.

Next, an electron transport layer (ETL) is formed on the emission layer by using (utilizing) various suitable methods, for example, vacuum deposition, spin coating, or casting. When the electron transport layer is formed using (utilizing) vacuum deposition or spin coating, the deposition and coating conditions may be similar to those for the formation of the hole injection layer, though the conditions for deposition and coating may vary according to the material that is used (utilized) to form the electron transport layer. A material for forming the electron transport layer may stably transport electrons provided from an electron injection electrode (cathode), and may be a suitable electron transportation material. Examples of suitable electron transport materials are a quinoline derivative, such as tris(8-quinolinolate) aluminum ($Alq_3$), TAZ, Balq, beryllium bis (benzoquinolin-10-olate) ($Bebq_2$), ADN, Compound 201, and Compound 202, but are not limited thereto.

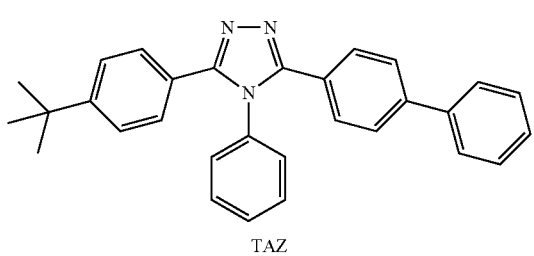

TAZ

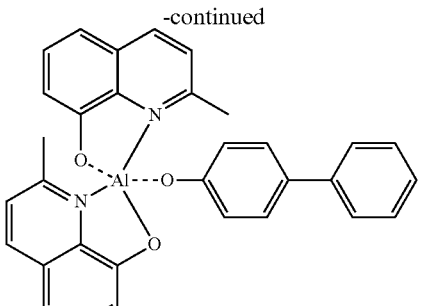

BAlq

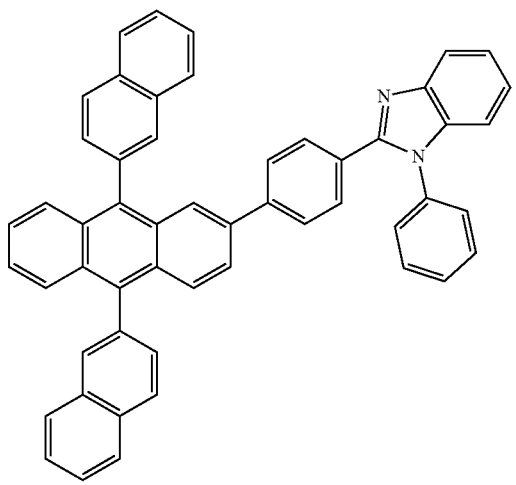

Compound 201

Compound 202

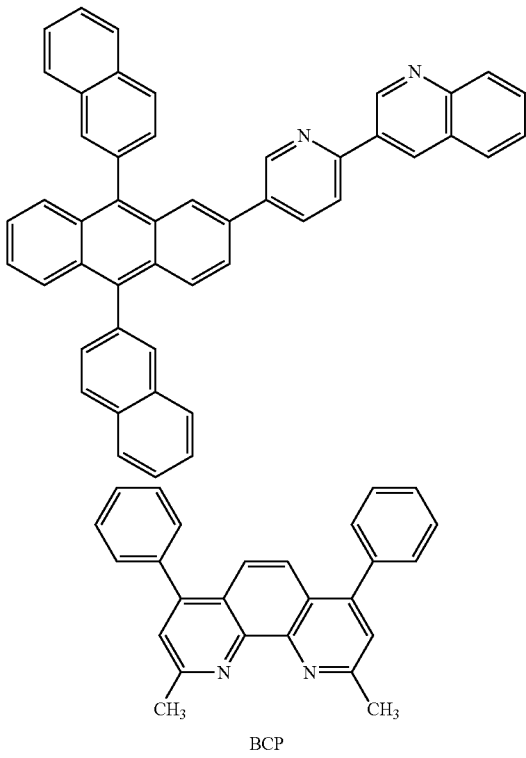

BCP

A thickness of the electron transport layer may be in a range of about 100 Å to about 1,000 Å, for example, about 150 Å to about 500 Å. In one embodiment, when the thickness of the electron transport layer is within the ranges described above, the electron transport layer has satisfactory electron transport characteristics without a substantial increase in driving voltage.

Also, the electron transport layer may include, in addition to an electron transport organic compound, a metal-containing material.

The metal-containing material may include a Li complex. Non-limiting examples of the Li complex are lithium quinolate (LiQ) and Compound 203 illustrated below:

Compound 203

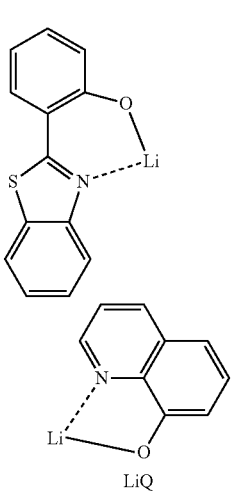

LiQ

Then, an electron injection layer (EIL), which facilitates injection of electrons from the cathode, may be formed on the electron transport layer. Any suitable electron injection material may be used (utilized) to form the electron injection layer.

Non-limiting examples of materials for forming the electron injection layer are LiF, NaCl, CsF, $Li_2O$, and BaO, which are known in the art. The deposition conditions of the electron injection layer may be similar to those used (utilized) to form the hole injection layer, although the deposition conditions may vary according to the material that is used (utilized) to form the electron injection layer.

A thickness of the electron injection layer may be in a range of about 1 Å to about 100 Å, for example, about 3 Å to about 90 Å. In one embodiment, when the thickness of the electron injection layer is within the ranges described above, the electron injection layer has satisfactory electron injection characteristics without a substantial increase in driving voltage.

The second electrode 17 is disposed on the organic layer 15. The second electrode may be a cathode that is an electron injection electrode, and in this regard, a metal for forming the second electrode 17 may be a material having a low work function, and such a material may be metal, an alloy, an electrically conductive compound, or a mixture thereof. For example, lithium (Li), magnesium (Mg), aluminum (Al), aluminum-lithium (Al—Li), calcium (Ca), magnesium-indium (Mg—In), or magnesium-silver (Mg—Ag) may be formed as a thin film to obtain a transmissive electrode. Also, to manufacture a top emission light-emitting device, a transmissive electrode may be formed using (utilizing) ITO or IZO.

Hereinbefore, the organic light-emitting device has been described with reference to the drawing, but is not limited thereto.

In addition, when a phosphorescent dopant is used (utilized) in the emission layer, a triplet exciton or a hole may diffuse to the electron transport layer. To reduce or prevent the diffusion, a hole blocking layer (HBL) may be formed between the hole transport layer and the emission layer or between the H-functional layer and the emission layer by vacuum deposition, spin coating, casting, LB deposition, or the like. When the hole blocking layer is formed by vacuum deposition or spin coating, the deposition or coating conditions may be similar to those applied to form the hole injection layer, although the deposition or coating conditions may vary according to the material that is used (utilized) to form the hole blocking layer. A hole blocking material may be any one of suitable hole blocking materials, and examples thereof are an oxadiazole derivative, a triazole derivative, a phenanthroline derivative, and so on. For example, BCP illustrated below may be used (utilized) as the hole-blocking material.

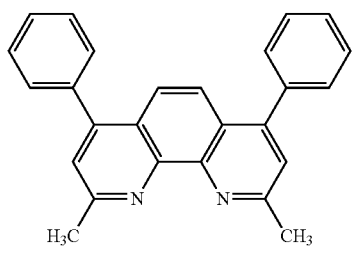

BCP

A thickness of the hole blocking layer may be in a range of about 20 Å to about 1,000 Å, for example, about 30 Å to about 300 Å. In one embodiment, when the thickness of the hole blocking layer is within these ranges, the hole blocking layer has excellent hole blocking characteristics without a substantial increase in driving voltage.

Hereinafter, an organic light-emitting device according to an embodiment is described in more detail with reference to Synthesis Examples and Examples. However, the organic light-emitting device is not limited thereto.

The $C_1$-$C_{60}$ alkyl group used herein refers to a linear or branched $C_1$-$C_{60}$ alkyl group, such as a methyl group, an ethyl group, a propyl group, an isobutyl group, a sec-butyl group, a pentyl group, an iso-amyl group, or a hexyl group; and the substituted $C_1$-$C_{60}$ alkyl group is formed by substituting at least one hydrogen atom of the $C_1$-$C_{60}$ alkyl group with one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_6$-$C_{60}$ aryl group, a $C_2$-$C_{60}$ heteroaryl group, —N($Q_{11}$)($Q_{12}$), —Si($Q_{13}$)($Q_{14}$)($Q_{15}$), and B($Q_{16}$)($Q_{17}$) (where $Q_{11}$ to $Q_{17}$ may be each independently selected from a hydrogen, a $C_1$-$C_{60}$ alkyl group, a $C_2$-$C_{60}$ alkenyl group, a $C_2$-$C_{60}$ alkynyl group, a $C_6$-$C_{60}$ aryl group, and a $C_2$-$C_{60}$ heteroaryl group).

The $C_1$-$C_{60}$ alkoxy group used herein refers to a group represented by the formula -OA (wherein A is the $C_1$-$C_{60}$ alkyl group described above), and non-limiting examples thereof are a methoxy group, an ethoxy group, and an isopropyloxy group, and one or more hydrogen atoms of these alkoxy groups may be substituted with the same substituents as described in connection with the substituted $C_1$-$C_{60}$ alkyl group.

The $C_2$-$C_{60}$ alkenyl group used herein refers to a $C_2$-$C_{60}$ alkyl group that has at least one carbon-carbon double bond in the middle or end thereof. Examples thereof are an ethenyl group, a prophenyl group, and a butenyl group. At least one hydrogen atom of these $C_2$-$C_{60}$ alkenyl groups may be substituted with the same substituents as described in connection with the substituted $C_1$-$C_{60}$ alkyl group.

The $C_2$-$C_{60}$ alkynyl group used herein refers to a $C_2$-$C_{60}$ alkyl group that has at least one carbon-carbon triple bond in the middle or end thereof. Examples of the $C_2$-$C_{60}$ alkynyl group are an ethynl group and a propynyl group. One or more hydrogen atoms of these alkynyl groups may be substituted with the same substituents as described in connection with the substituted $C_1$-$C_{60}$ alkyl group.

The $C_6$-$C_{60}$ aryl group used herein refers to a monovalent group having a carbocyclic aromatic system having 6 to 60 carbon atoms including at least one aromatic ring. The unsubstituted $C_6$-$C_{60}$ arylene group is a divalent group having a carbocyclic aromatic system having 6 to 60 carbon atoms including at least one aromatic ring. When the aryl group and the arylene group have at least two rings, they may be fused to each other. One or more hydrogen atoms of the aryl group and the arylene group may be substituted with the same substituents as described in connection with the substituted $C_1$-$C_{60}$ alkyl group.

The $C_2$-$C_{60}$ heteroaryl group used herein refers to a monovalent group having a system constituted with one or more aromatic rings having at least one hetero atom selected from nitrogen (N), oxygen (O), phosphorous (P), silicon (Si), and sulfur (S) as the ring-forming atom, and carbon atoms as the remaining ring-forming atoms. The $C_2$-$C_{60}$ heteroarylene group used herein refers to a divalent group having a system constituted with one or more aromatic rings having at least one hetero atom selected from nitrogen (N), oxygen (O), phosphorous (P), silicon (Si), and sulfur (S) as the ring-forming atom, and carbon atoms as the remaining ring-forming atoms. In this regard, when the heteroaryl group and the heteroarylene group each include two or more rings, the rings may be fused to each other. One or more hydrogen atoms of the heteroaryl group and the heteroarylene group may be substituted with the same substituents as described in connection with the substituted $C_1$-$C_{60}$ alkyl group.

Examples of the $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoan imidazolyl group, an imidazo pyridinyl group, and an imidazo pyrimidinyl group. Examples of the unsubstituted $C_2$-$C_{60}$ hetroarylene group may be easily understood by referring to examples of the substituted or unsubstituted $C_2$-$C_{60}$ heteroaryl group.

The $C_6$-$C_{60}$ aryloxy group used herein refers to a group represented by the formula -$OA_2$ (wherein $A_2$ is the $C_6$-$C_{60}$ aryl group), and a $C_6$-$C_{60}$ arylthio group used herein refers to a group represented by the formula -$SA_3$ (wherein $A_3$ is the $C_6$-$C_{60}$ aryl group).

EXAMPLE

Synthesis Example 1: Synthesis of Compound 1

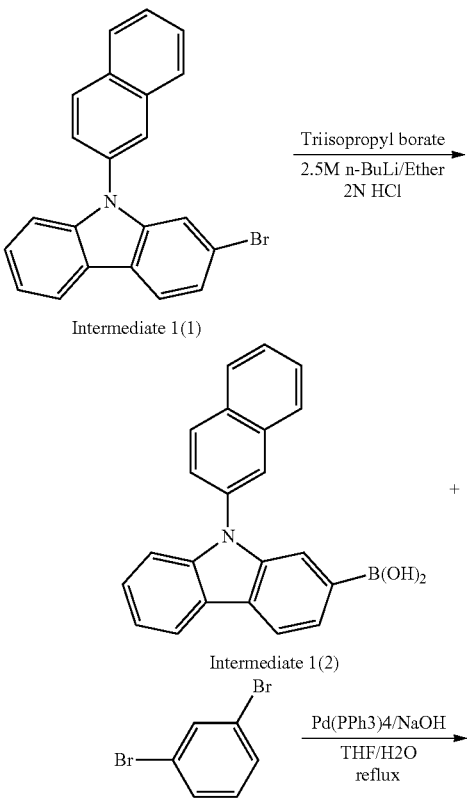

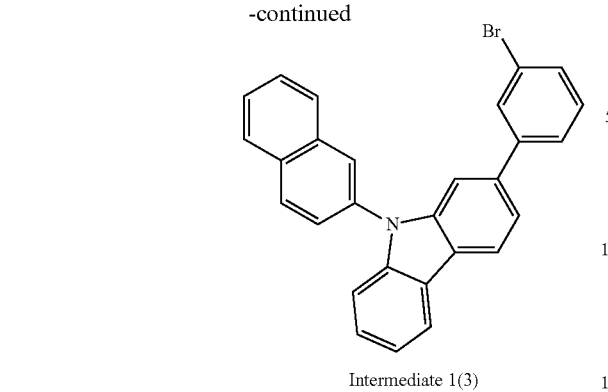

Intermediate 1(3)

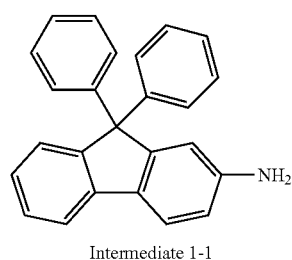

Intermediate 1-1

+

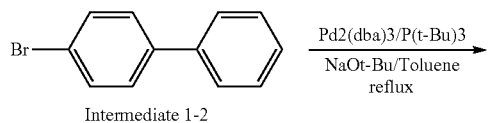

Intermediate 1-2

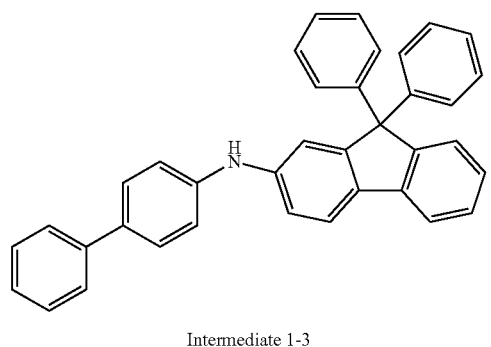

Intermediate 1-3

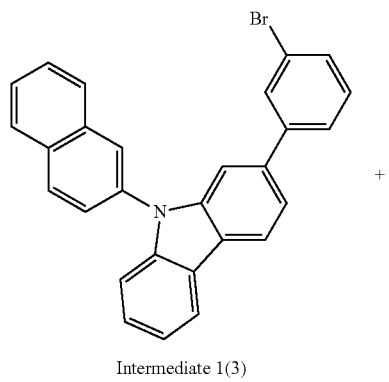

Intermediate 1(3)

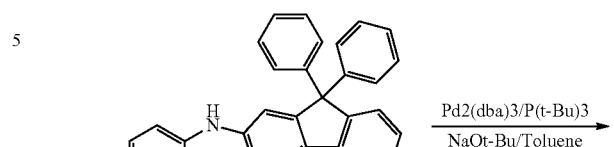

Intermediate 1-3

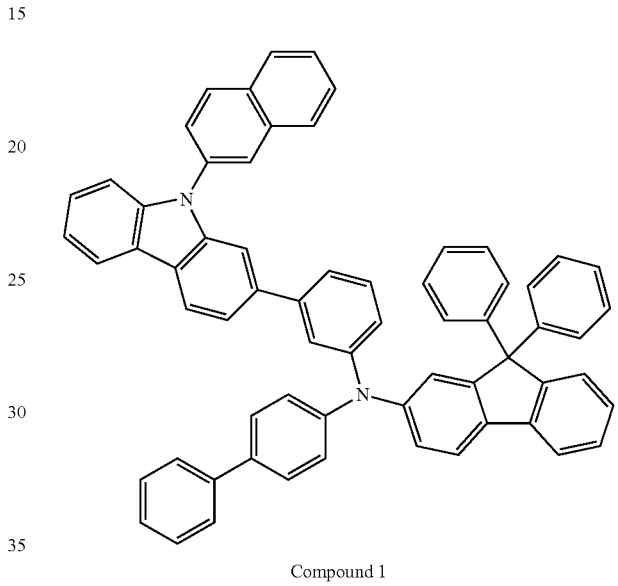

Compound 1

Synthesis of Intermediate 1(2)

Intermediate 1(1) (1 eq.) was dissolved in an anhydrous ether, the temperature of the reaction product was dropped to −78° C., n-BuLi (2.5 M in hexane) (1.1 eq.) was slowly added dropwise thereto, and the reaction product was stirred for 30 minutes. Then, the reaction product was cooled to a temperature of −78° C., triisopropylborate (1.5 eq.) was added dropwise thereto, the resultant product was stirred at room temperature, and then diluted by using (utilizing) water. 2N HCl was added thereto. When the reaction stopped, an organic layer extracted by using (utilizing) ethyl acetate and water was dried with MgSO$_4$, concentrated, and then, silicagel column chromatography was performed on the obtained organic material, which was then re-crystallized to obtain Intermediate 1(2).

Synthesis of Intermediate 1(3)

Intermediate 1(2) (1 eq.) was dissolved in THF, and then, 1,3-dibromobenzene (1.1 eq.), Pd(PPh$_3$)$_4$ (0.03 eq.), NaOH (3 eq.), and water were added thereto. The mixture was refluxed while being stirred. When the reaction stopped, an organic layer extracted by using (utilizing) ether and water was dried and concentrated by using (utilizing) MgSO$_4$, and then, silicagel column chromatography was performed on the obtained organic material, which was then re-crystallized to obtain Intermediate 1(3).

Synthesis of Intermediate 1-3

Intermediate 1-1 (1 eq.), Intermediate 1-2 (1.1 eq.), Pd$_2$(dba)$_3$ (0.05 eq.), P(t-Bu)$_3$ (0.1 eq.), NaOt-Bu (3 eq.), and toluene (10.5 mL/1 mmol starting material) were added to a round-bottomed flask, and then, reacted with each other at a temperature of 100° C. When the reaction stopped, an organic layer extracted by using (utilizing) ether and water was dried and concentrated by using (utilizing) MgSO$_4$, and then, silicagel column chromatography was performed on the obtained organic material, which was then re-crystallized to obtain Intermediate 1-3.

Synthesis of Compound 1

Intermediate 1(3) (1 eq.), Intermediate 1-3 (1.1 eq.), Pd$_2$(dba)$_3$ (0.05 eq.), P(t-Bu)$_3$ (0.1 eq.), NaOt-Bu (3 eq.), and toluene (10.5 mL/1 mmol starting material) were added to a round-bottomed flask, and then, the reaction was performed thereon at a temperature of 100° C. When the reaction stopped, an organic layer extracted by using (utilizing) ether and water was dried and concentrated by using (utilizing) MgSO$_4$, and then, silicagel column chromatography was performed on the obtained organic material, which was then re-crystallized to obtain Compound 1.

Synthesis Example 2: Synthesis of Compound 2

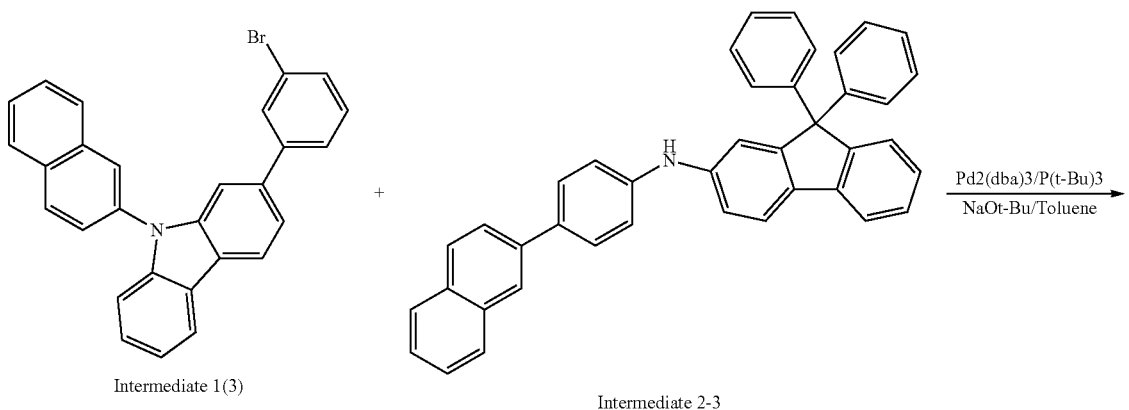

Compound 2

Intermediate 2-3 was synthesized in the same manner as used (utilized) to synthesize Intermediate 1-3 in Synthesis Example 1, except that in synthesizing Intermediate 1-3, 2-(4-bromophenyl)naphthalene was used (utilized) instead of Intermediate 1-2. Compound 2 was synthesized in the same manner as used (utilized) to synthesize Compound 1 in Synthesis Example 1 except that in synthesizing Compound 1, Intermediate 2-3 was used (utilized) instead of Intermediate 1-3.

Synthesis Example 3: Synthesis of Compound 3

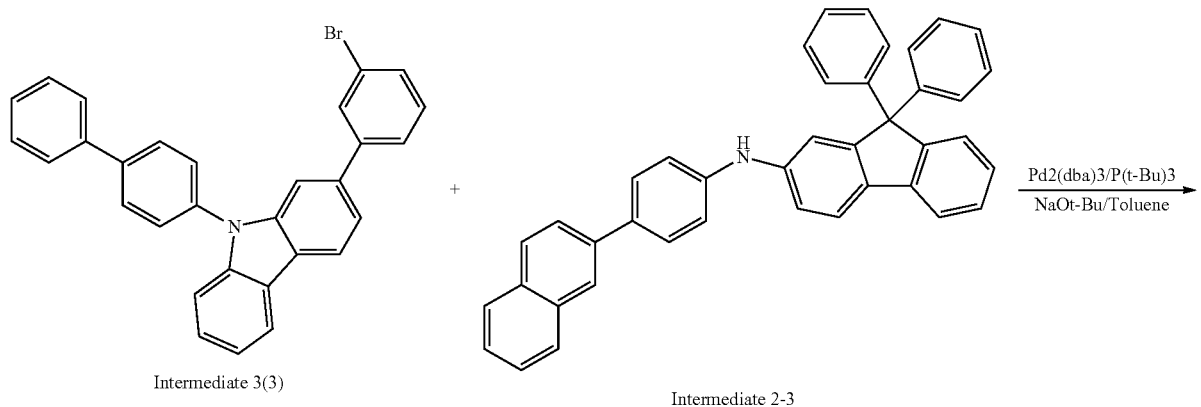

Intermediate 3(3)

Intermediate 2-3

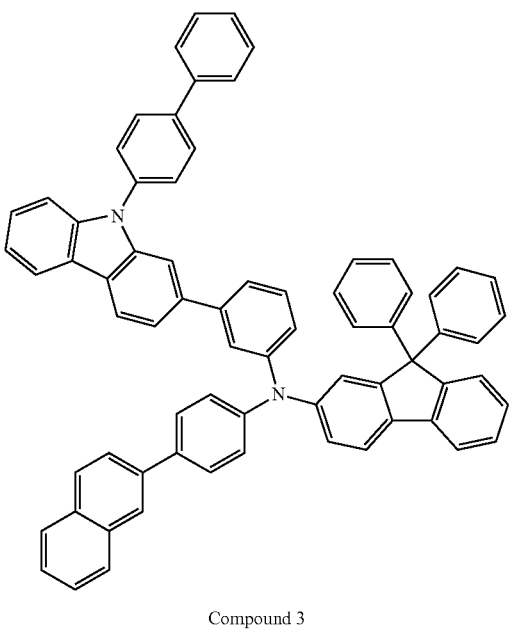

Compound 3

Intermediate 3(3) was synthesized in the same manner as used (utilized) to synthesize Intermediate 1(3) in Synthesis Example 1, except that in synthesizing Intermediate 1(3), Intermediate 3(1) was used (utilized) instead of Intermediate 1(1). Intermediate 2-3 was synthesized in the same manner as used (utilized) to synthesize Intermediate 1-3 in Synthesis Example 1, except that in synthesizing Intermediate 1-3, 2-(4-bromophenyl)naphthalene was used (utilized) instead of Intermediate 1-2. Compound 3 was synthesized in the same manner as used (utilized) to synthesize Compound 1 in Synthesis Example 1, except that in synthesizing Compound 1, Intermediate 3(3) and Intermediate 2-3 were respectively used (utilized) instead of Intermediate 1(3) and Intermediate 1-3.

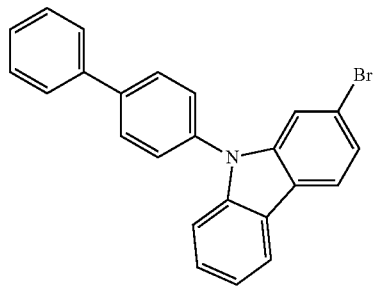

Intermediate 3(1)

Synthesis Example 4: Synthesis of Compound 4

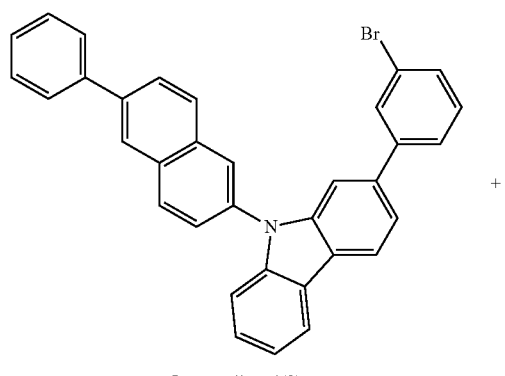

Intermediate 4(3)

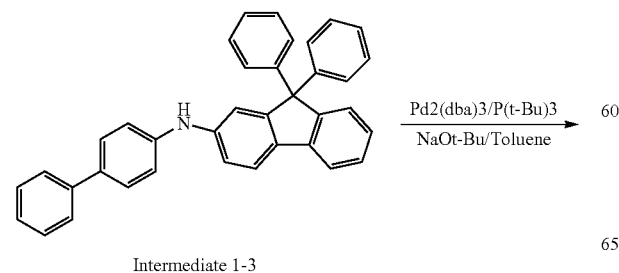

Intermediate 1-3

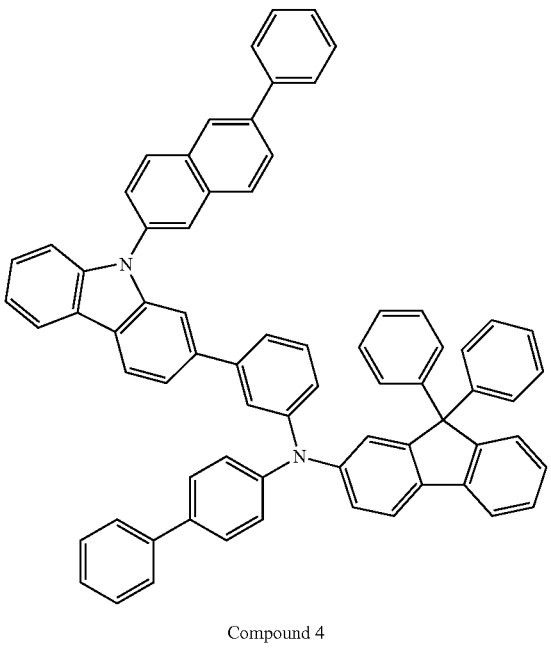

Compound 4

Intermediate 4(3) was synthesized in the same manner as used (utilized) to synthesize Intermediate 1(3) in Synthesis Example 1, except that in synthesizing Intermediate 1(3), Intermediate 4(1) was used (utilized) instead of Intermediate 1(1). Compound 4 was synthesized in the same manner as used (utilized) to synthesize Compound 1 in Synthesis Example 1 except that in synthesizing Compound 1, Intermediate 4(3) was used (utilized) instead of Intermediate 1(3).

Intermediate 4(1)

Synthesis Example 5: Synthesis of Compound 5

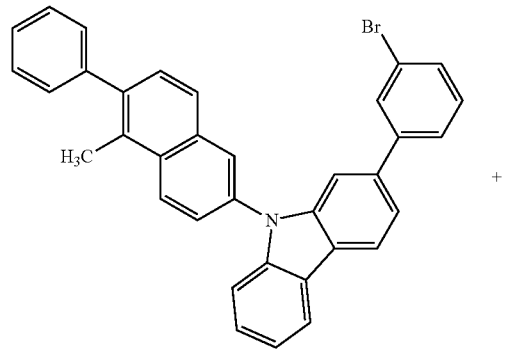

Intermediate 5(3)

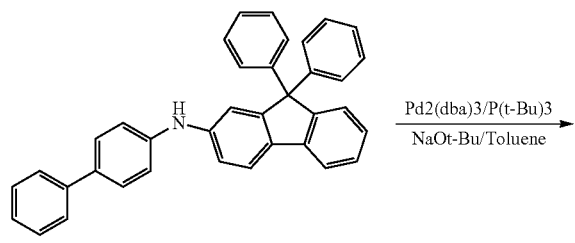

Intermediate 1-3

Pd2(dba)3/P(t-Bu)3
NaOt-Bu/Toluene

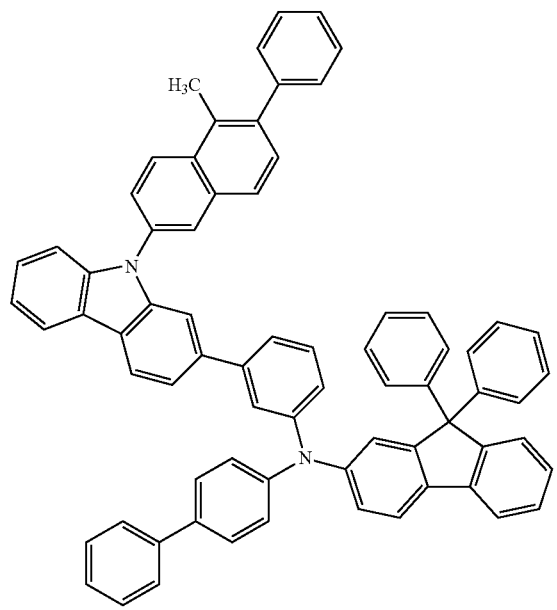

Compound 5

Intermediate 5(3) was synthesized in the same manner as used (utilized) to synthesize Intermediate 1(3) in Synthesis Example 1, except that in synthesizing Intermediate 1(3), Intermediate 5(1) was used (utilized) instead of Intermediate 1(1). Compound 5 was synthesized in the same manner as used (utilized) to synthesize Compound 1 in Synthesis Example 1 except that in synthesizing Compound 1, Intermediate 5(3) was used (utilized) instead of Intermediate 1(3).

Intermediate 5(1)

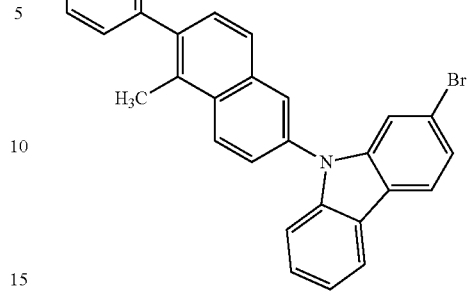

Synthesis Example 6: Synthesis of Compound 6

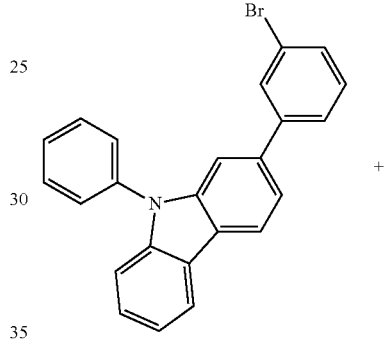

Intermediate 6(3)

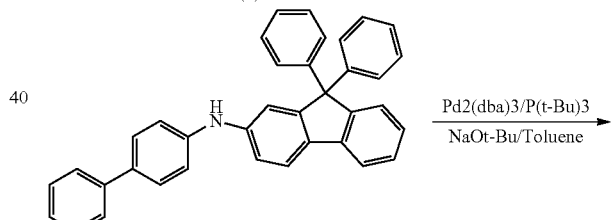

Intermediate 1-3

Pd2(dba)3/P(t-Bu)3
NaOt-Bu/Toluene

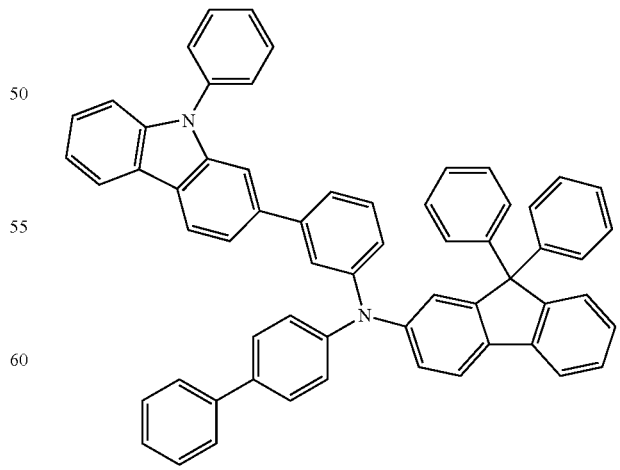

Compound 6

Intermediate 6(3) was synthesized in the same manner as used (utilized) to synthesize Intermediate 1(3) in Synthesis Example 1, except that in synthesizing Intermediate 1(3), Intermediate 6(1) was used (utilized) instead of Intermediate 1(1). Compound 6 was synthesized in the same manner as used (utilized) to synthesize Compound 1 in Synthesis Example 1 except that in synthesizing Compound 1, Intermediate 6(3) was used (utilized) instead of Intermediate 1(3).

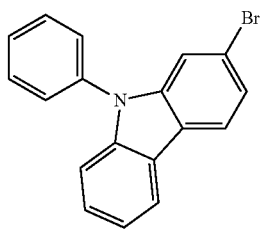

Intermediate 6(1)

Synthesis Example 7: Synthesis of Compound 7

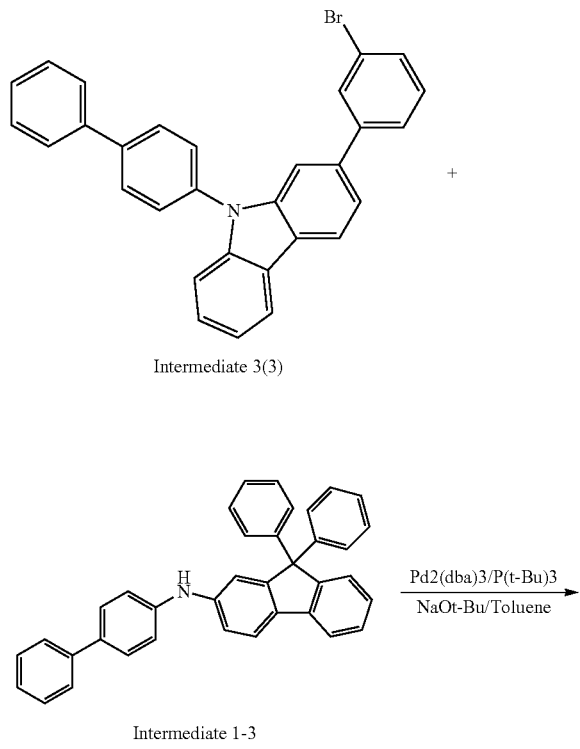

Intermediate 3(3)

Intermediate 1-3

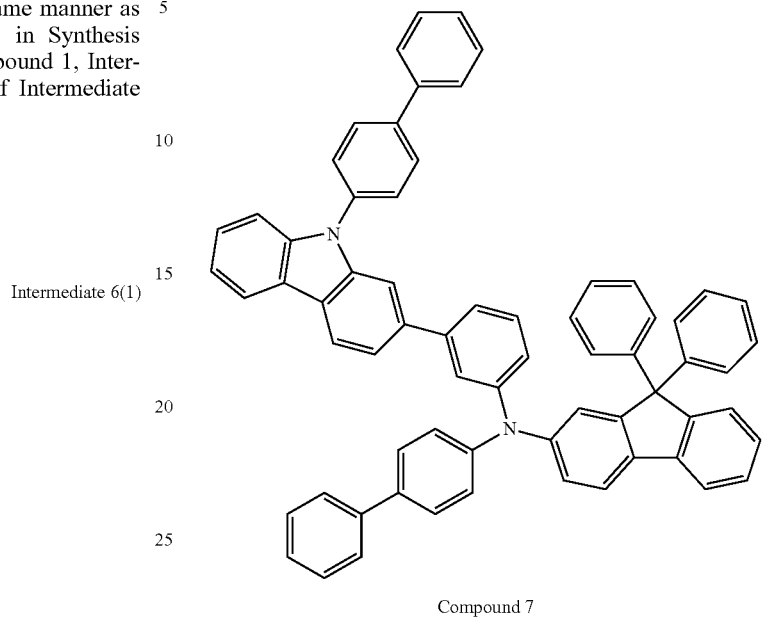

Compound 7

Compound 7 was synthesized in the same manner as used (utilized) to synthesize Compound 1 of Synthesis Example 1, except that Intermediate 3(3) was used (utilized) instead of Intermediate 1(3).

Example 1

An anode was prepared by cutting a substrate (with ITO/Ag/ITO having a thickness of 70/1000/70 Å deposited thereon) to a size of 50 mm×50 mm×0.7 mm, ultrasonically cleaning the glass substrate by using (utilizing) isopropyl alcohol for 5 minutes and pure water for 5 minutes, irradiating UV light for 30 minutes thereto and exposing to ozone to clean. Then, the anode was loaded into a vacuum deposition apparatus.

Compound 1 was deposited on the structure of ITO/Ag/ITO (anode) to form a hole transport layer having a thickness of 1400 Å, and then, ADN (host) and BD1(dopant) were co-deposited on the hole transport layer at a ratio of 97:3 to form an emission layer having a thickness of 200 Å.

Compound 201 and LiQ were deposited at a weight ratio of 1:1 as an electron transport compound on the emission layer to form an electron transport layer having a thickness of 360 Å, LiQ was deposited on the electron transport layer to form an electron injection layer having a thickness of 5 Å, and Mg and Ag were deposited on the electron injection layer at a weight ratio of 90:10 to form a cathode having a thickness of 130 Å, thereby completing the manufacture of an organic light-emitting device.

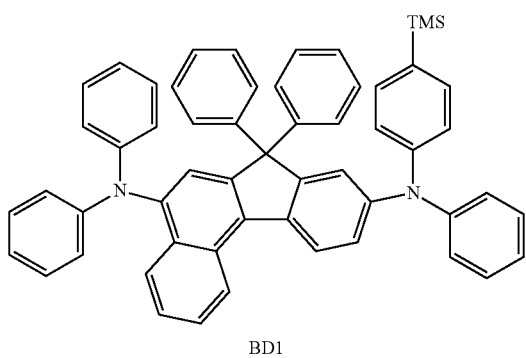

BD1

Example 2

An organic light-emitting device was manufactured in the same manner as in Example 1, except that in forming a hole transport layer, Compound 2 was used (utilized) instead of Compound 1.

Example 3

An organic light-emitting device was manufactured in the same manner as in Example 1, except that in forming a hole transport layer, Compound 3 was used (utilized) instead of Compound 1.

Comparative Example 1

An organic light-emitting device was manufactured in the same manner as in Example 1, except that in forming a hole transport layer, Compound A was used (utilized) instead of Compound 1.

Comparative Example 2

An organic light-emitting device was manufactured in the same manner as in Example 1, except that in forming a hole transport layer, Compound B was used (utilized) instead of Compound 1.

Evaluation Example 1

The driving voltage, current density, brightness, power, and color purity of the organic light-emitting devices manufactured according to Examples 1 to 3 and Comparative Examples 1 and 2 were measured by using (utilizing) Kethley SMU 236 and a brightness photometer PR650.

TABLE 1

| | Material for hole transport layer | Driving voltage (V) | Current density (mA/cm$^2$) | Brightness (cd/A) | Power (lm/W) | CIE_x | CIE_y |
|---|---|---|---|---|---|---|---|
| Example 1 | Compound 1 | 4.1 | 10.7 | 6.8 | 5.2 | 0.142 | 0.054 |
| Example 2 | Compound 2 | 3.8 | 10.5 | 6.7 | 5.6 | 0.141 | 0.054 |
| Example 3 | Compound 3 | 4.2 | 10.5 | 6.8 | 5.0 | 0.142 | 0.055 |
| Comparative Example 1 | Compound A | 4.6 | 11.4 | 5.9 | 4.0 | 0.140 | 0.051 |

TABLE 1-continued

| | Material for hole transport layer | Driving voltage (V) | Current density (mA/cm$^2$) | Brightness (cd/A) | Power (lm/W) | CIE_x | CIE_y |
|---|---|---|---|---|---|---|---|
| Comparative Example 2 | Compound B | 5.1 | 14.9 | 5.3 | 3.3 | 0.135 | 0.060 |

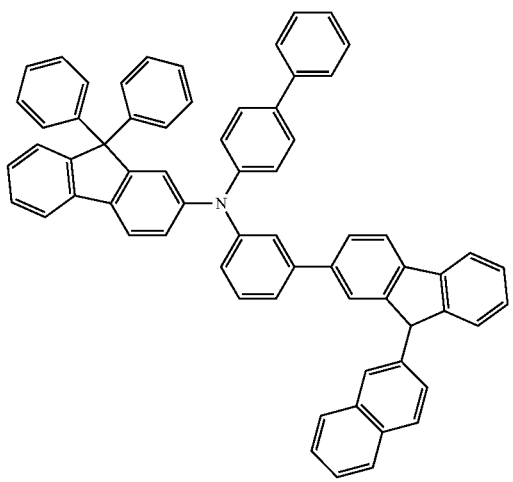

1

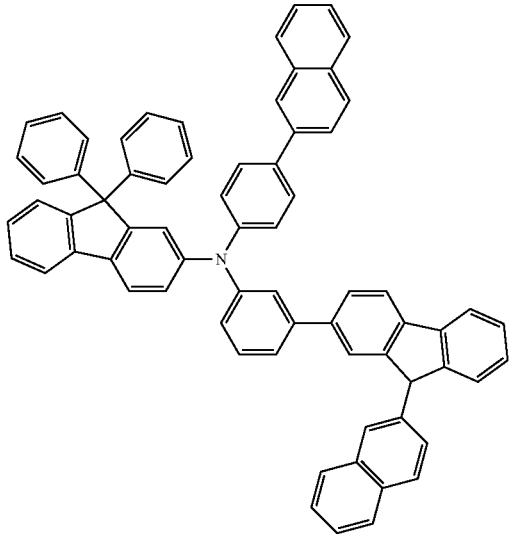

2

TABLE 1-continued

| Material for hole transport layer | Driving voltage (V) | Current density (mA/cm$^2$) | Brightness (cd/A) | Power (lm/W) | CIE_x | CIE_y |
|---|---|---|---|---|---|---|

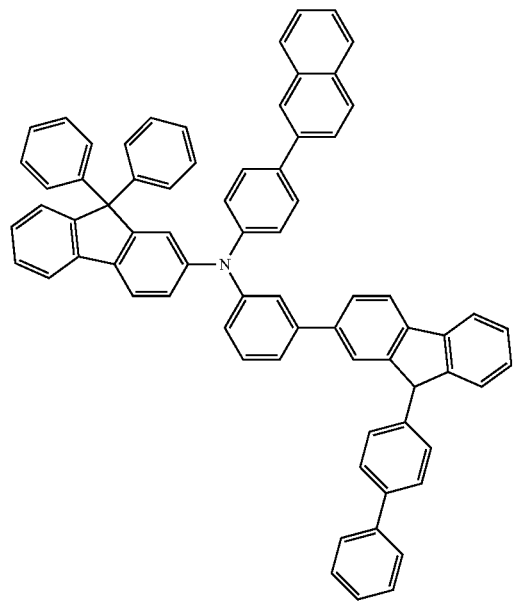

3

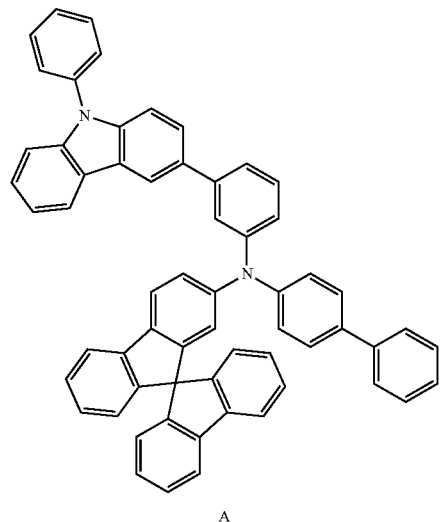

A

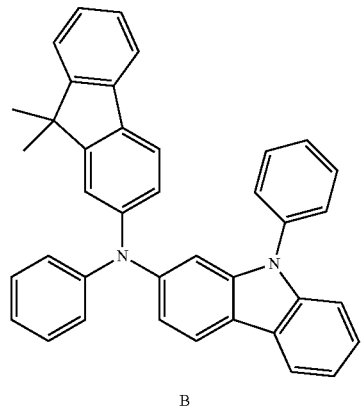

B

From Table 1 above, it was confirmed that the organic light-emitting devices of Examples 1 to 3 had excellent driving voltage, current density, brightness, power, and color purity, compared with the organic light-emitting devices of Comparative Examples 1 and 2.

An organic light-emitting device including the amine-based compound according to an embodiment may have a low driving voltage, high efficiency, high color purity, and long lifespan.

It should be understood that the example embodiments described herein should be considered in a descriptive sense only and not for purposes of limitation. Descriptions of features or aspects within each embodiment should typically be considered as available for other similar features or aspects in other embodiments.

While one or more embodiments of the present invention have been described with reference to the drawing, it will be understood by those of ordinary skill in the art that various changes in form and details may be made therein without departing from the spirit and scope of the present invention as defined by the following claims, and equivalents thereof.

What is claimed is:

1. An amine-based compound represented by Formula 1A below:

wherein in

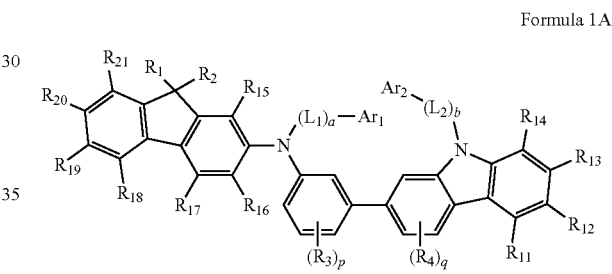

Formula 1A $L_1$ and $L_2$ are each independently selected from:
a phenylene group, a naphthylene group, a fluorenylene group, a spiro-fluorenylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, an isoindolylene group, an indolylene group, a quinolinylene group, a benzoquinolinylene group, a quinoxalinylene group, a quinazolinylene group, a cinnolinylene group, a carbazolylene group, and a triazinylene group; and
a phenylene group, a naphthylene group, a fluorenylene group, a spiro-fluorenylene group, a phenanthrenylene group, an anthracenylene group, a fluoranthenylene group, a triphenylenylene group, a pyrenylene group, a chrysenylene group, a pyridinylene group, a pyrazinylene group, a pyrimidinylene group, a pyridazinylene group, an isoindolylene group, an indolylene group, a quinolinylene group, a benzoquinolinylene group, a quinoxalinylene group, a quinazolinylene group, a cinnolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a and b are each independently 0 or 1;

$Ar_1$ and $Ar_2$ are each independently selected from:

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

$R_1$ and $R_2$ are each independently selected from:

a $C_1$-$C_{20}$ alkyl group;

a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;

$R_3$, $R_4$ and $R_{11}$ to $R_{21}$ are each independently selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, and a $C_1$-$C_{20}$ alkyl group; and p and q are each independently 0, 1, or 2, wherein at least one of $Ar_1$, $Ar_2$, $R_1$ to $R_4$, and $R_{11}$ to $R_{21}$ is selected from:

a naphthyl group;

a naphthyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and a phenyl group, an anthracenyl group, and a fluorenyl group, each substituted with at least one naphthyl group.

2. The amine-based compound of claim 1, wherein Ar$_1$ and Ar$_2$ are each independently a group represented by one of Formulae 3-1 to 3-20 below:

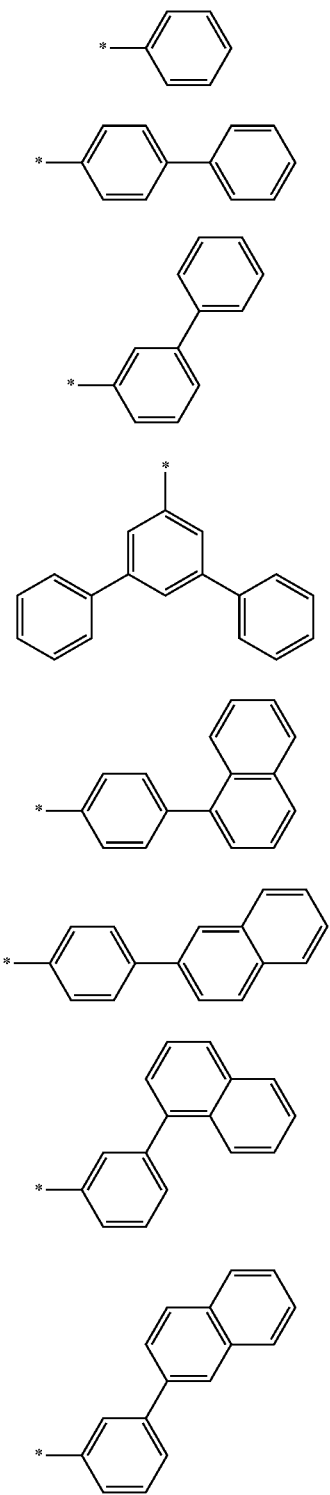

Formula 3-1

Formula 3-2

Formula 3-3

Formula 3-4

Formula 3-5

Formula 3-6

Formula 3-7

Formula 3-8

-continued

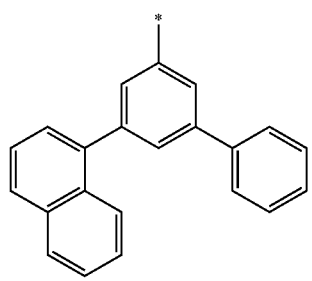

Formula 3-9

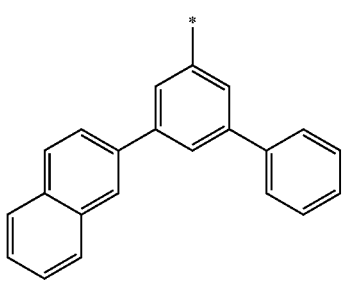

Formula 3-10

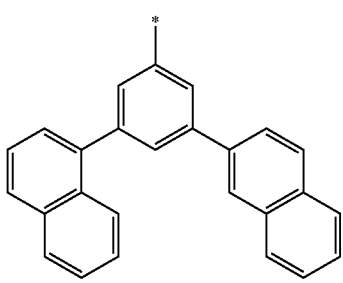

Formula 3-11

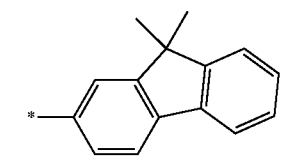

Formula 3-12

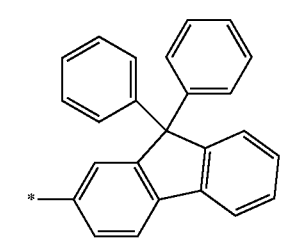

Formula 3-13

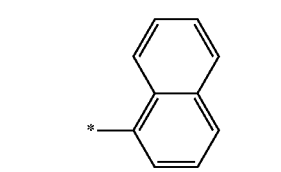

Formula 3-14

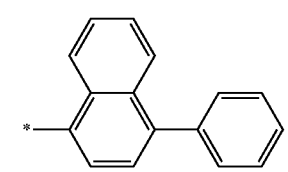

Formula 3-15

-continued

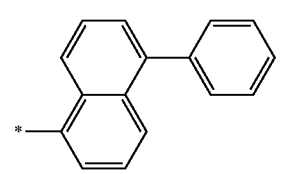
Formula 3-16

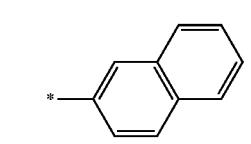
Formula 3-17

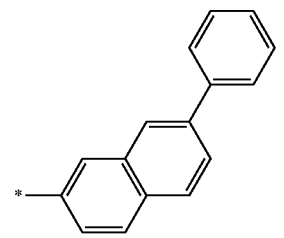
Formula 3-18

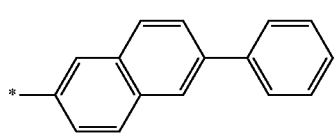
Formula 3-19

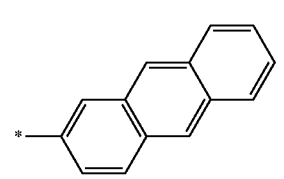
Formula 3-20 and
in Formulae 3-1 to 3-20, * indicates a binding site to N, $L_1$, or $L_2$ of Formula 1.

3. The amine-based compound of claim 1, wherein $R_1$ and $R_2$ are each independently selected from:
an ethyl group, a propyl group, a butyl group, a pentyl group, a hexyl group, a heptyl group;
a $C_1$-$C_{20}$ alkyl group substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;
a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group; and
a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group.

4. The amine-based compound of claim 1, wherein
$R_1$ and $R_2$ are each independently selected from an ethyl group, a propyl group, a butyl group, a pentyl group, a hexyl group, a heptyl group, and groups represented by Formulae 3-1 to 3-20:

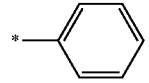
Formula 3-1

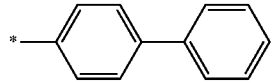
Formula 3-2

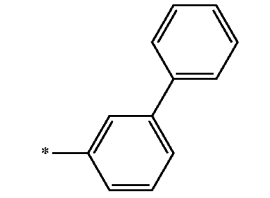
Formula 3-3

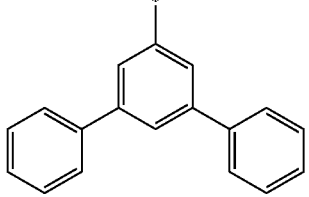
Formula 3-4

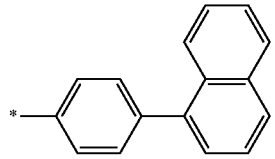
Formula 3-5

83
-continued

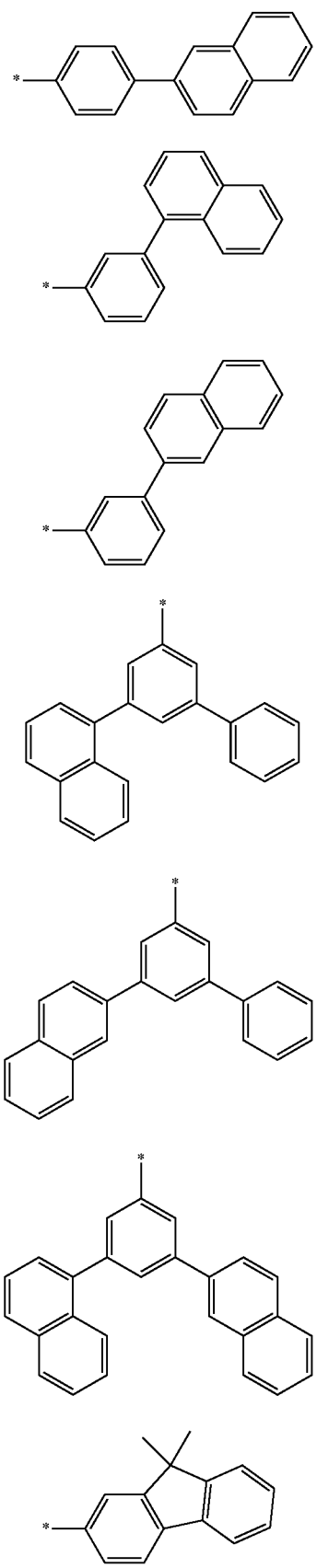

Formula 3-6

Formula 3-7

Formula 3-8

Formula 3-9

Formula 3-10

Formula 3-11

Formula 3-12

84
-continued

Formula 3-13
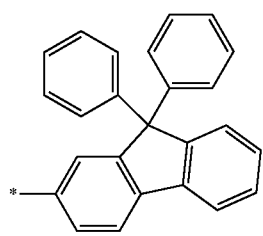

Formula 3-14
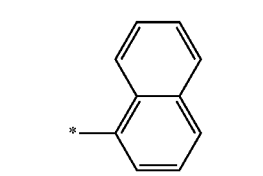

Formula 3-15
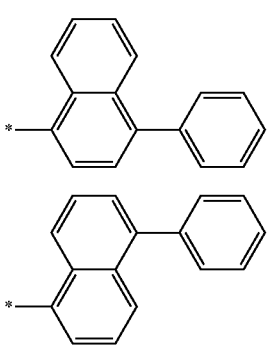

Formula 3-16

Formula 3-17
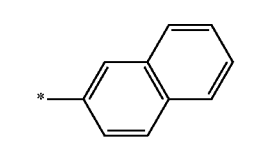

Formula 3-18
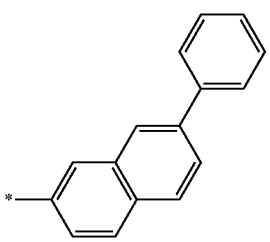

Formula 3-19
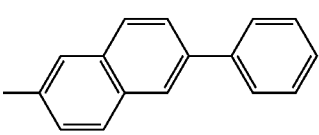

Formula 3-20
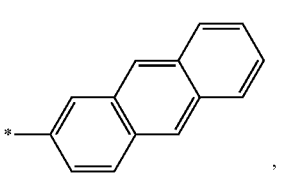

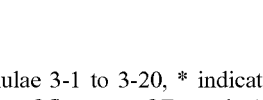

and in Formulae 3-1 to 3-20, * indicates a binding site to a carbon of fluorene of Formula 1.

5. The amine-based compound of claim 1, wherein $R_3$, $R_4$, and $R_{11}$ to $R_{21}$ in Formula 1A are each independently selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a propyl group, a butyl group, a pentyl group, a hexyl group, a heptyl group, and groups represented by Formulae 3-1 to 3-20:

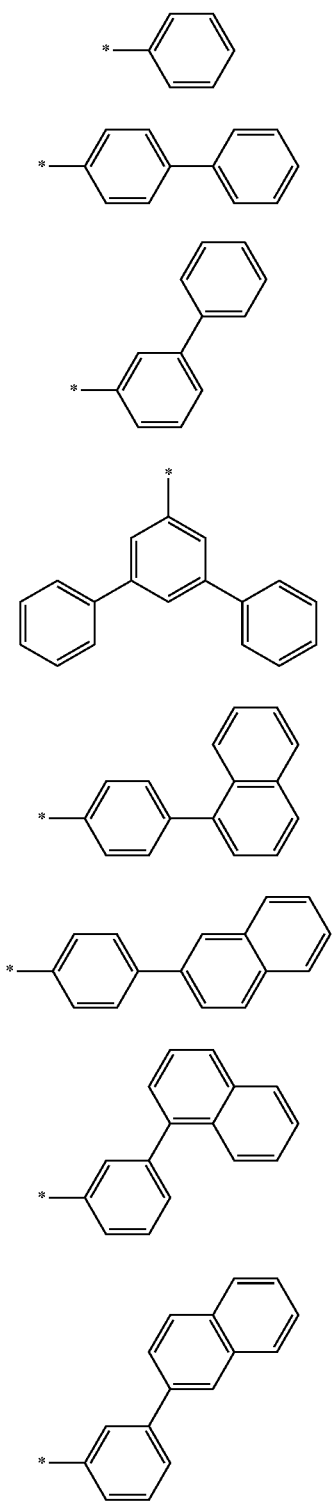

Formula 3-1

Formula 3-2

Formula 3-3

Formula 3-4

Formula 3-5

Formula 3-6

Formula 3-7

Formula 3-8

Formula 3-9

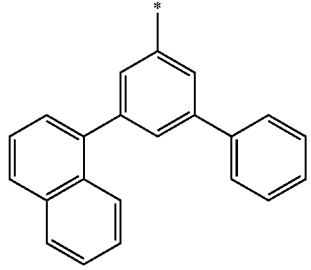

Formula 3-10

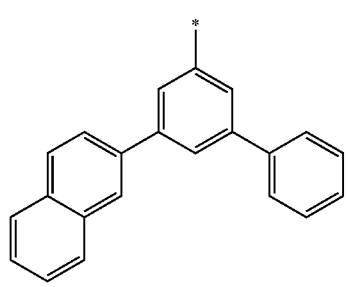

Formula 3-11

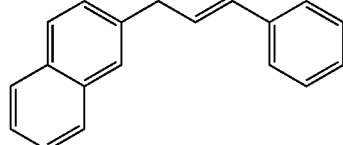

Formula 3-12

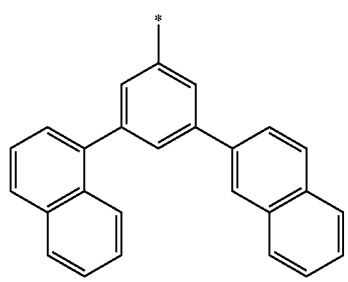

Formula 3-14

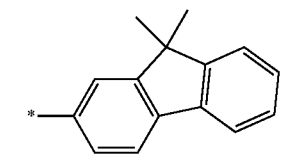

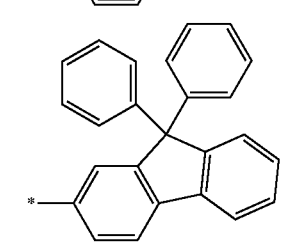

Formula 3-15

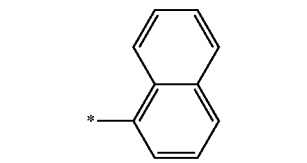

-continued

Formula 3-16
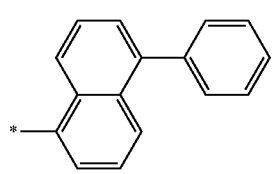

Formula 3-17
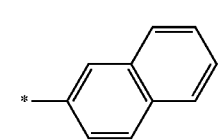

Formula 3-18
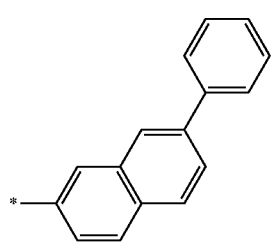

Formula 3-19
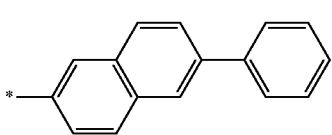

Formula 3-20
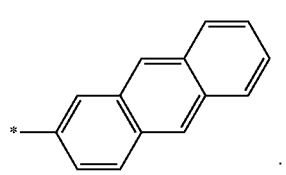

6. The amine-based compound of claim 1, wherein
$L_1$ and $L_2$ are each independently selected from:
a phenylene group, a naphthylene group, and a fluorenylene group; and
a phenylene group, a naphthylene group, and a fluorenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a phenanthrenyl group, an anthracenyl group, a fluoranthenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, a benzoquinolinyl group, a quinoxalinyl group, a quinazolinyl group, a cinnolinyl group, a carbazolyl group, and a triazinyl group;
a and b are each independently 0 or 1;
$Ar_1$ and $Ar_2$ are each independently selected from the groups represented by Formulae 3-1 to 3-20 below;
$R_1$ and $R_2$ are each independently selected from a methyl group, an ethyl group, a propyl group, a butyl group, a pentyl group, a hexyl group, a heptyl group, and the groups represented by Formulae 3-1 to 3-20;
$R_3$, $R_4$, and $R_{11}$ to $R_{21}$ in Formula 1A are each independently selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a propyl group, a butyl group, a pentyl group, a hexyl group, a heptyl group, and the groups represented by Formulae 3-1 to 3-20;
p and q are each independently 0, 1, or 2; and
at least one of $Ar_1$, $Ar_2$, $R_1$ to $R_4$, and $R_{11}$ to $R_{21}$ are represented by one of Formulae 3-5 to 3-11 and 3-14 to 3-19, Formula 3-1
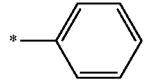

Formula 3-2
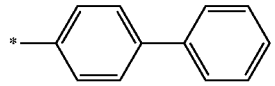

Formula 3-3
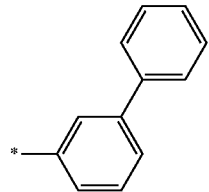

Formula 3-4
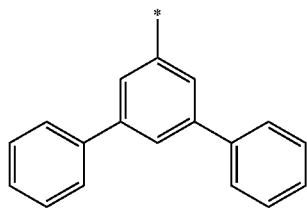

Formula 3-5
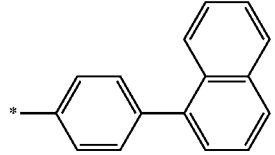

Formula 3-6
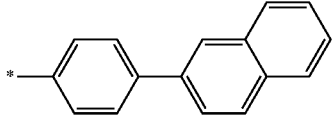

Formula 3-7
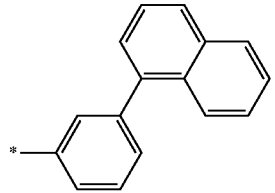

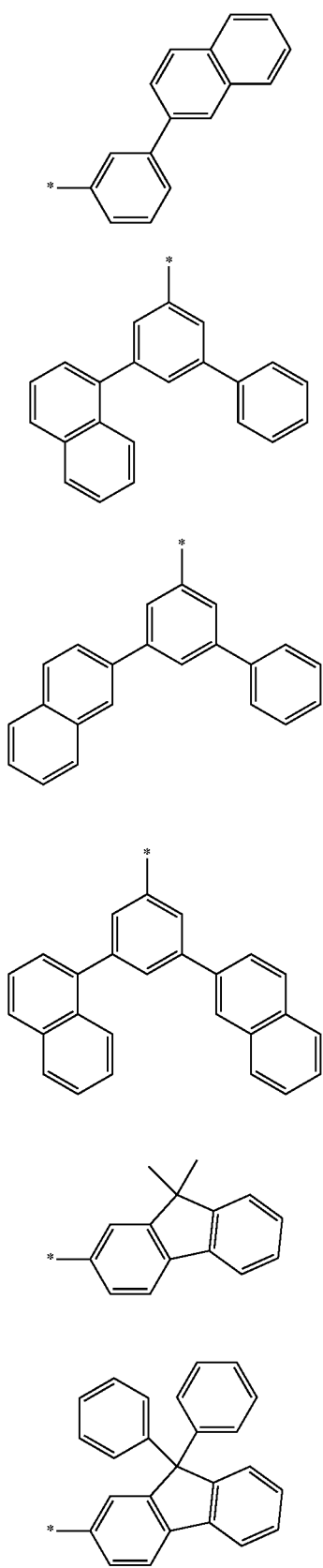
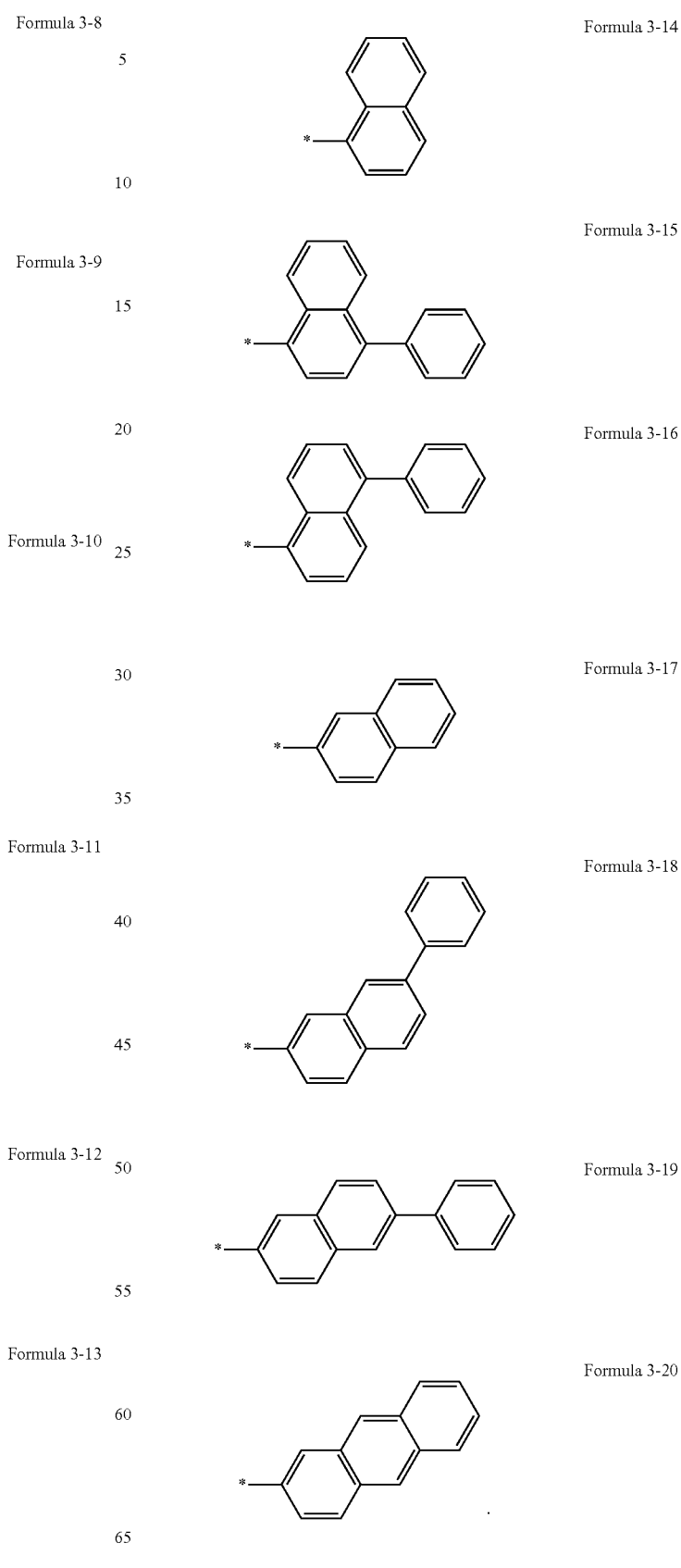
Formula 3-8
Formula 3-9
Formula 3-10
Formula 3-11
Formula 3-12
Formula 3-13
Formula 3-14
Formula 3-15
Formula 3-16
Formula 3-17
Formula 3-18
Formula 3-19
Formula 3-20

7. An amine-based compound selected from one of Compounds 1 to 7 below:
1
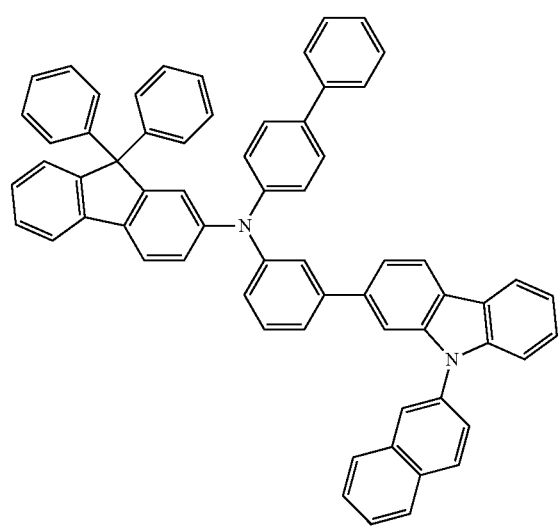
2
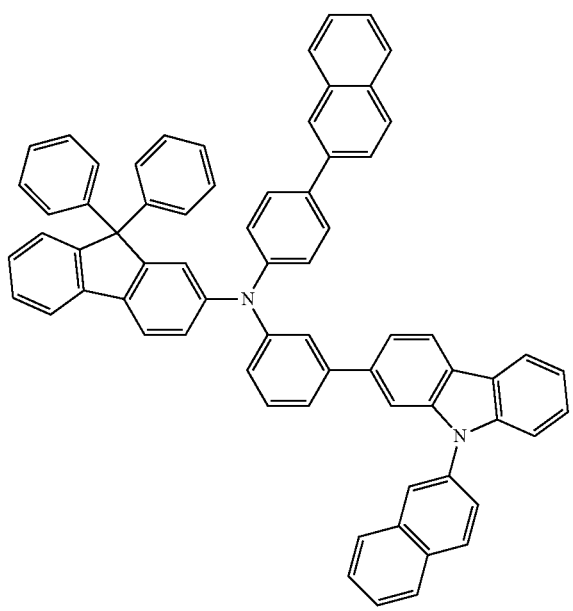
3
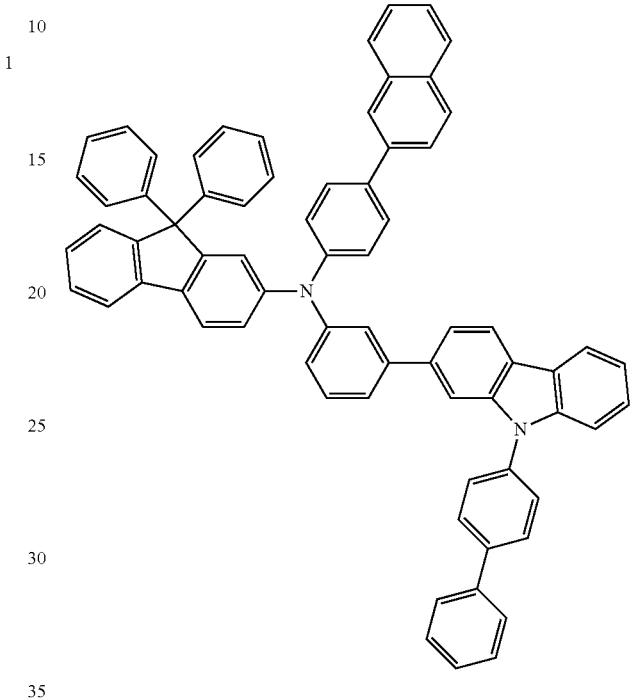
4
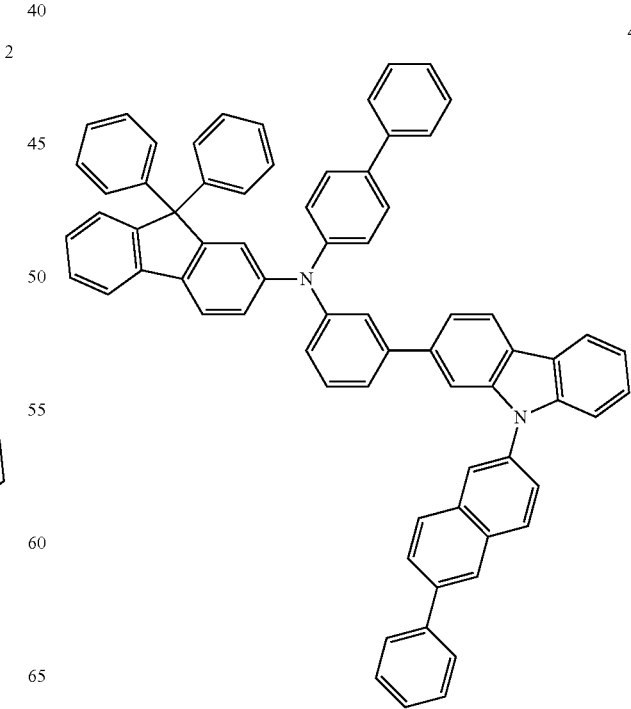

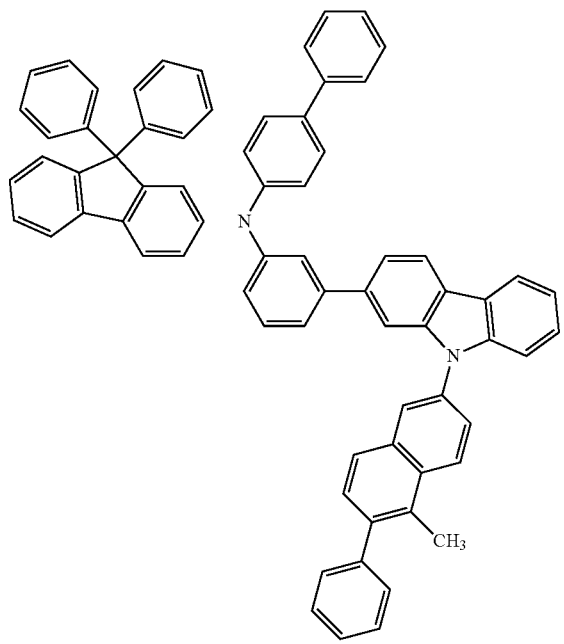

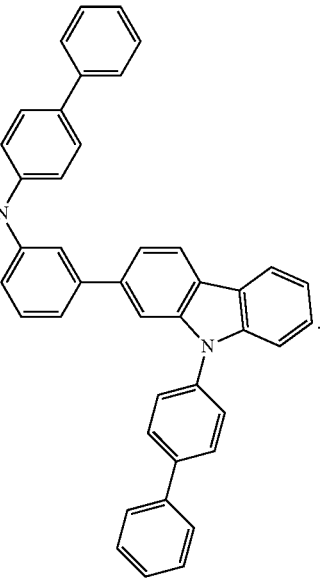

8. An organic light-emitting device comprising:
a first electrode;
a second electrode facing the first electrode; and
an organic layer between the first electrode and the second electrode and comprising an emission layer, wherein the organic layer comprises at least one amine-based compound of claim 1.

9. The organic light-emitting device of claim 8, wherein the organic layer comprises:
i) a hole transport region between the first electrode and the emission layer and comprising at least one selected from a hole injection layer, a hole transport layer, a functional layer having a hole injection capability and a hole transport capability, a buffer layer, and an electron blocking layer; and
ii) an electron transport region between the emission layer and the second electrode and comprising at least one selected from a hole blocking layer, an electron transport layer, and an electron injection layer.

10. The organic light-emitting device of claim 9, wherein the hole transport region comprises the amine-based compound.

11. The organic light-emitting device of claim 10, wherein the hole transport region further comprises a p-dopant.

* * * * *